(12) United States Patent
Sato et al.

(10) Patent No.: US 6,911,526 B2
(45) Date of Patent: Jun. 28, 2005

(54) COMPOUNDS THAT INHIBIT THE INTERACTION BETWEEN SIGNAL-TRANSDUCING PROTEINS AND THE GLGF (PDZ/DHR) DOMAIN AND USES THEREOF

(75) Inventors: Takaaki Sato, Fort Lee, NJ (US); Junn Yanagisawa, Fort Lee, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 08/681,219

(22) Filed: Jul. 22, 1996

(65) Prior Publication Data

US 2002/0058607 A1 May 16, 2002

(51) Int. Cl.[7] .............................. C07K 7/08; C07K 7/06; C07K 14/705
(52) U.S. Cl. ...................... 530/326; 530/300; 530/317; 530/324; 530/325; 530/327; 530/328; 530/331; 530/350
(58) Field of Search ................................ 530/300, 331, 530/330, 328, 327, 326, 325, 317, 351, 329, 324, 350; 424/198.1; 514/2; 435/7.23

(56) References Cited

U.S. PATENT DOCUMENTS

| | | | | |
|---|---|---|---|---|
| 5,202,257 A | * | 4/1993 | Heinemann et al. | 435/252.3 |
| 5,632,994 A | * | 5/1997 | Reed et al. | 424/198.1 |
| 5,747,245 A | | 5/1998 | Reed et al. | |
| 5,783,666 A | * | 7/1998 | Albertsen et al. | 530/350 |
| 5,827,516 A | * | 10/1998 | Urban et al. | 424/93.21 |
| 5,876,939 A | | 3/1999 | Reed et al. | |
| 6,066,621 A | * | 5/2000 | Sela et al. | 514/15 |
| 6,184,205 B1 | * | 2/2001 | Sparks et al. | 514/13 |

FOREIGN PATENT DOCUMENTS

| | | | |
|---|---|---|---|
| JP | 9512598 | | 9/1999 |
| WO | WO 94/04171 | * | 3/1994 |
| WO | 9534661 | | 12/1995 |
| WO | WO 96/18641 | * | 6/1996 |
| WO | 9711091 | | 3/1997 |

OTHER PUBLICATIONS

Shin, J. et al Proc. Natl. Acad. Sci. USA, 88: 1918–1922, 1991.*
Parker et al., Proteins 25/2:253–260, Jun. 1996.*
Pal et al., Proteins 36/3:332–9.*
Okimoto et al. Genetics 130: 471–498, 1992.*
Desjardins et al., J. Mol. Biol. 212:599–634, 1990.*
Niethammer, M. et al. Interaction between the C terminus of NMDA receptor subunits and multiple members of the PSD–95 family of membrane–associated guanylate kinases. J. Neuroscience, 16(7): 2157–2163, Apr. 1996.*
Zhang et al, "A mouse Fas–associated protein with homology to the human MORT1–FADD protein is essential for Fas–induced apotosis" Mol. Cell Biol. vol. 16, no. 6, pp. 2756–2763, Jun. 1996.*
Boldin, M. P., et al. (1995) *J. Biol. Chem.* 270: 7795–7798 (Exhibit B).
Chao, M.V. and B.L. Hempstead (1995) *TINS* 18: 321–326 (Exhibit C).
Cho, K.–O. et al. (1992) Neuron 9: 929–942 (Exhibit D).
Doyle, D.A., et al. (1996) *Cell* 85: 1067–1076 (Exhibit E).
Itoh, N. and S. Nagata (1993) *J. Biol. Chem.* 268: 10932–10937 (Exhibit F).
Itoh, N., et al. (1991) *Cell* 66: 233–243 (Exhibit G).
Kim, E., et al. (1995) *Nature* 378: 85–88 (Exhitit H).
Kornau, H.–C. et al. (1995) *Science* 269: 1737–1740 (Exhibit I).
Maekawa, K., et al., (1994) *FEBS Letters* 337: 200–206 (Exhibit J).
Matsumine, A., et al. (1996) Science 272: 1020–1023 (Exhibit K).
McGahon, A.J., et al. (1995) *Meth. Cell Biol.* 46: 153–185 (Exhibit L).
Saras, J., et al. (1994) *J.Biol Chem.* 269: 24082–24088 (Exhibit M); and.
Sato, T., et al. (1995) *Science* 268: 411–415 (Exhibit N).
U.S. Appl. No. 09/230,111, Sato & Yanagisawa, filed May 17, 1999.

* cited by examiner

*Primary Examiner*—Alana M. Harris
*Assistant Examiner*—Anne L. Holleran
(74) *Attorney, Agent, or Firm*—John P. White; Cooper & Dunham LLP

(57) ABSTRACT

This invention provides for a composition capable of inhibiting specific binding between a signal-transducing protein and a cytoplasmic protein. This invention also provides a method of identifying a compound capable of inhibiting specific binding between a signal-transducing protein and a cytoplasmic protein. This invention also provides a method of inhibiting the proliferation of cancer cells. This invention also provides a method of treating cancer with a composition in an amount effective to result in an amount in apoptosis of the cells. This invention also provides a method of inhibiting the proliferation of virally infected cells. This invention also provides for a method of treating a virally-infected subject with a composition in an amount effective to result in apoptosis of the cells. This invention also provides for pharmaceutical compositions.

3 Claims, 21 Drawing Sheets

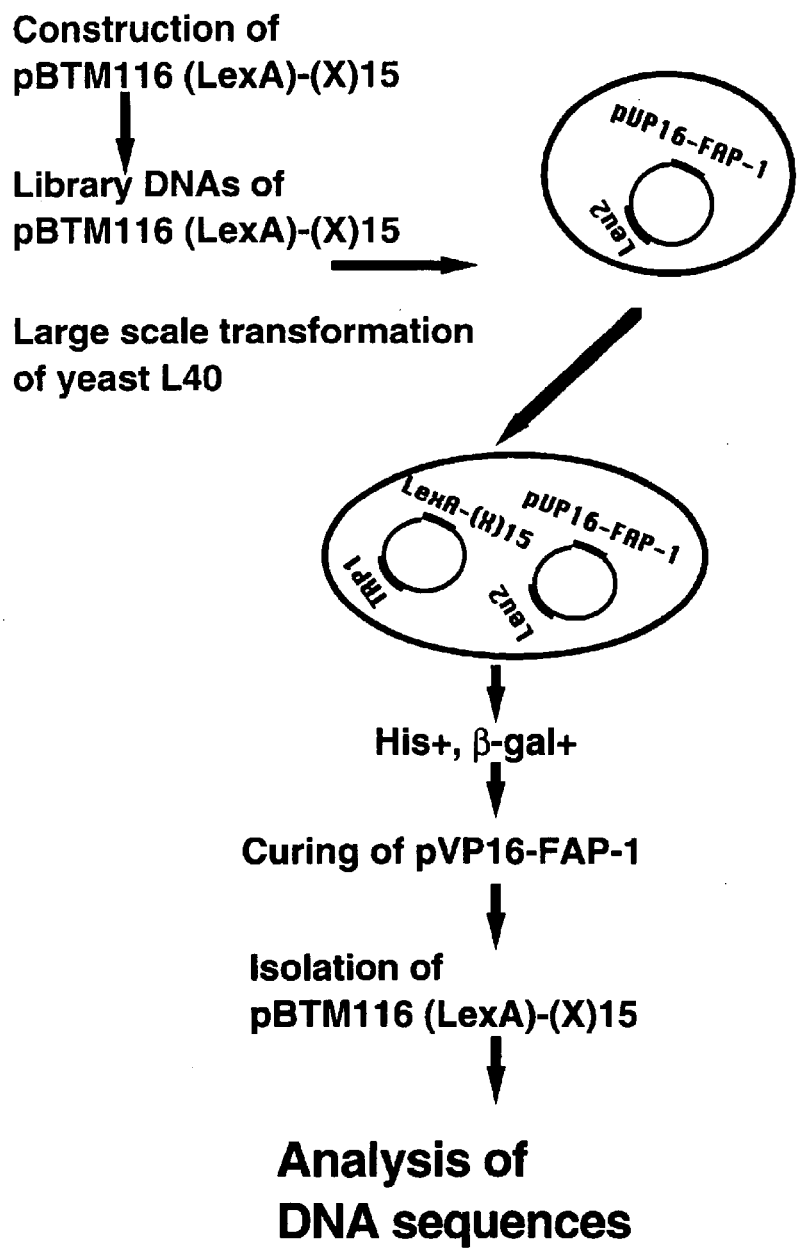

FIG. 2B

| | | | | | | | | | | | | | |
|---|---|---|---|---|---|---|---|---|---|---|---|---|---|
| Human | D | S | E | N | S | N | F | R | N | E | I | Q | S | L | V |

Rat: S I S N S R N E N E G Q S L E

Mouse: S T P D T G N E N E G Q C L E

| | | | | | | | | | | | | |
|---|---|---|---|---|---|---|---|---|---|---|---|---|
| C | Y | A | | | A | I | G | | L | | | | V | 12-0 |
| E | N | A | | | G | V | S | | E | | | | V | 5-0 |
| W | W | G | | | A | T | Q | | P | | | | V | 13-0 |
| E | H | A | | | Q | | Q | | Q | | | | V | 20-0 |
| N | S | S | | | F | H | S | | L | | | | V | 6-2 |
| G | L | R | | | L | P | P | | D | | | | V | 9-5 |
| G | S | D | | | S | G | V | | N | | | | V | 18-1 |
| D | K | K | | | R | P | V | | N | | | | V | 22-1 |
| T | G | K | | | D | V | W | | A | | | | V | 71-1 |
| A | S | R | | | N | E | E | | L | | | | I | 14-5 |

FIG. 2D

| | | | | | | | | | | | | | |
|---|---|---|---|---|---|---|---|---|---|---|---|---|---|
| I | P | P | D | S | E | D | G | N | E | E | Q | S | L | V | 8-1
| D | S | E | M | Y | N | F | R | S | Q | L | A | S | V | V | 9-3
| I | D | L | A | S | E | F | L | F | L | S | N | S | F | L | 14-1
| P | P | T | C | S | Q | A | N | S | G | R | I | S | T | L | 0-2

S D S N M N M N E L S E V   57-5
             Q N F R T Y I V S F V   72-1
                 R E T I E S T V   25-9
                   R G F I S S L V   16-13
                     T I Q S V I   6-3
                         E S L V   18-1

Consensus: *t* S-X-V/L/I

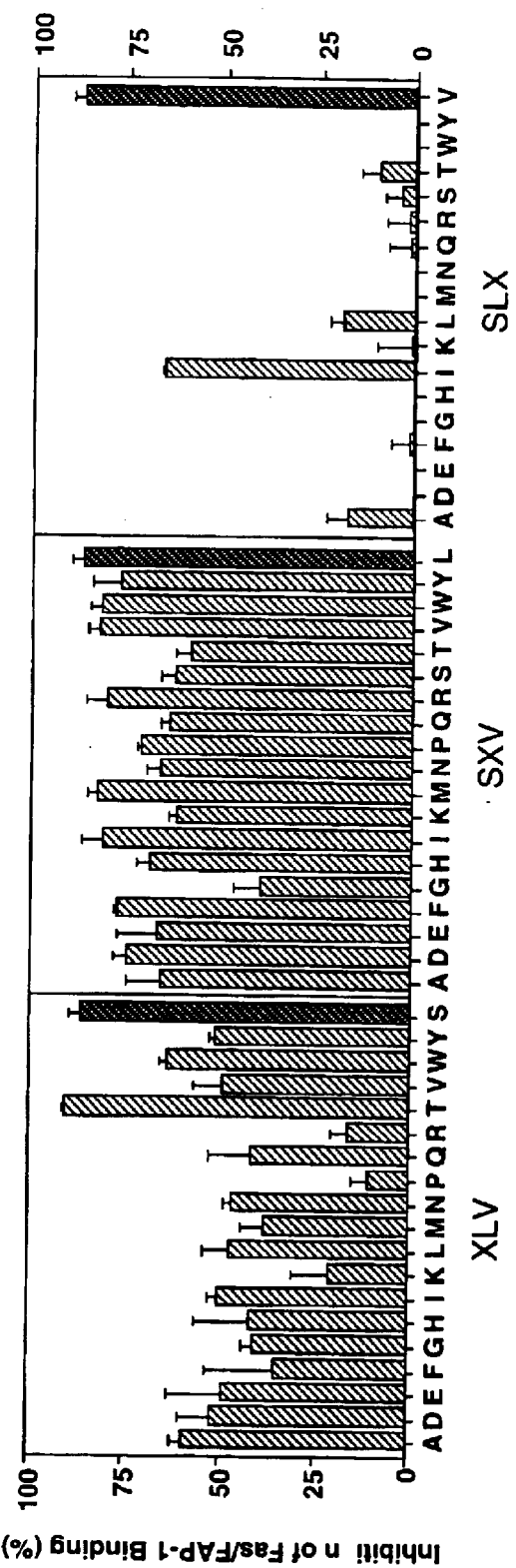

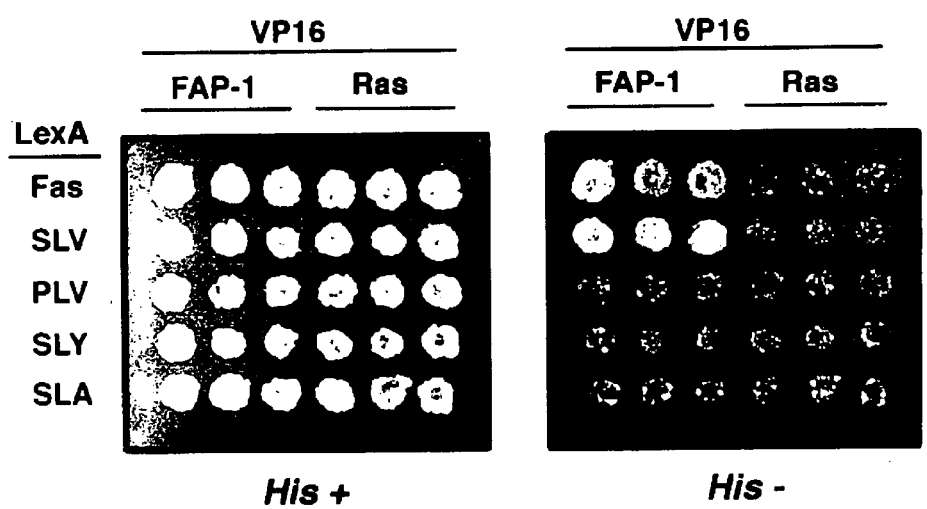

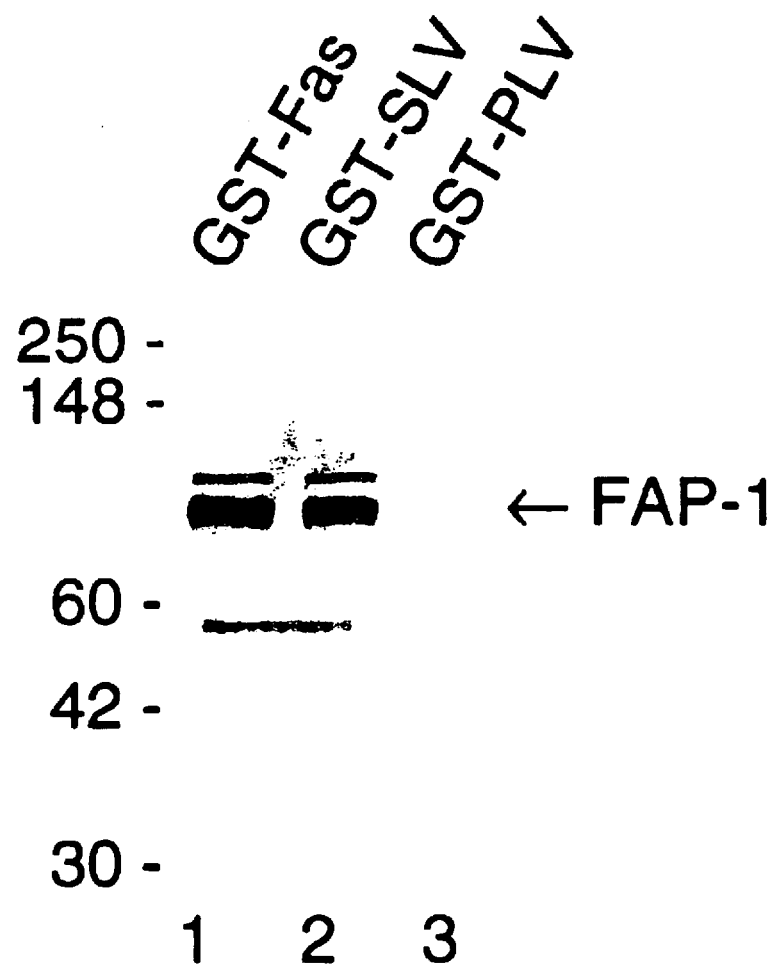

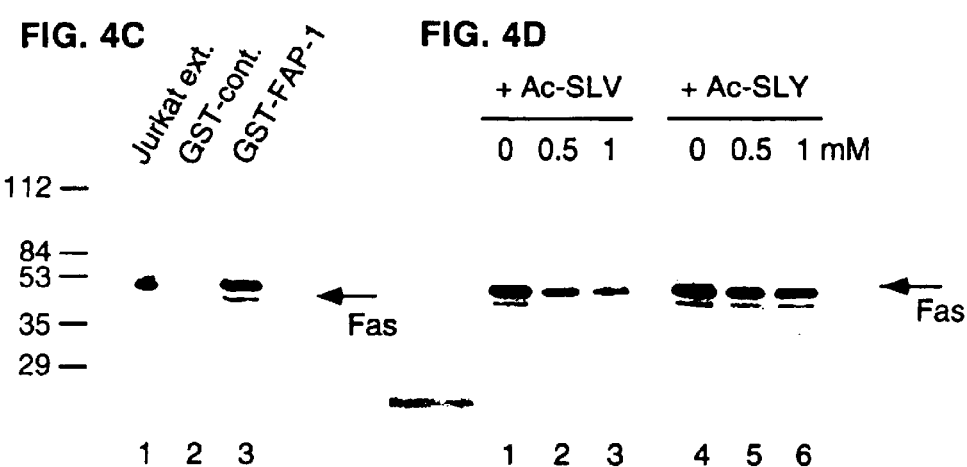

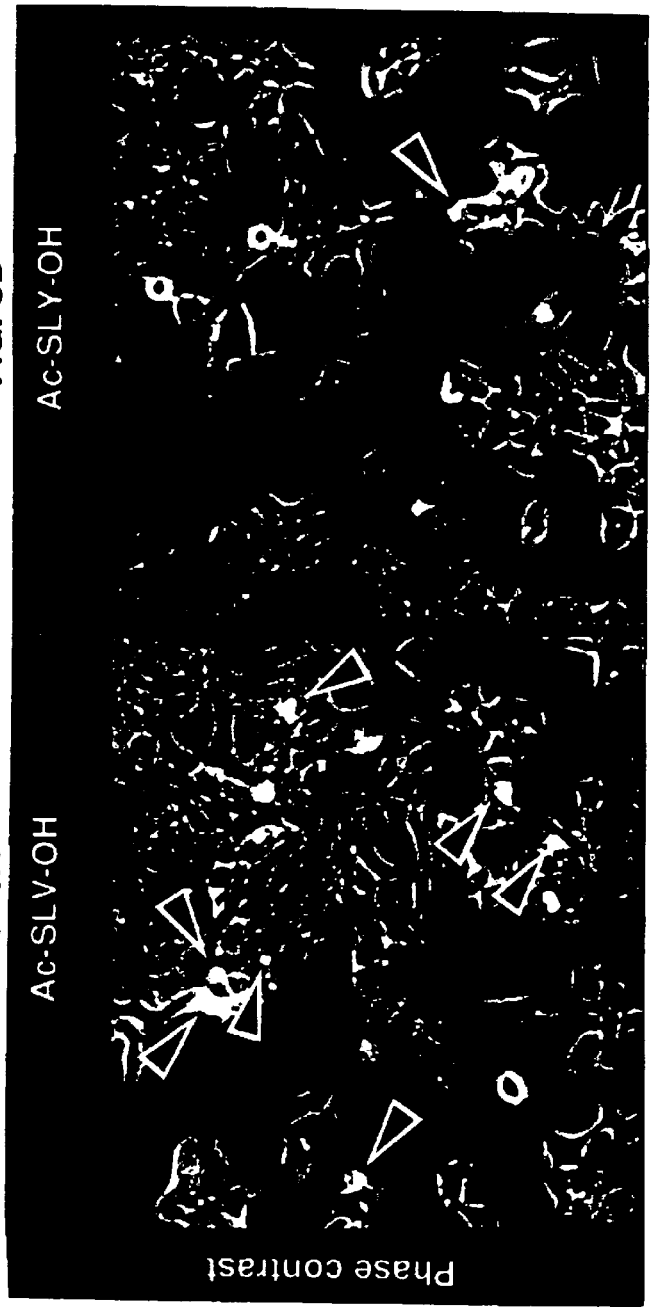

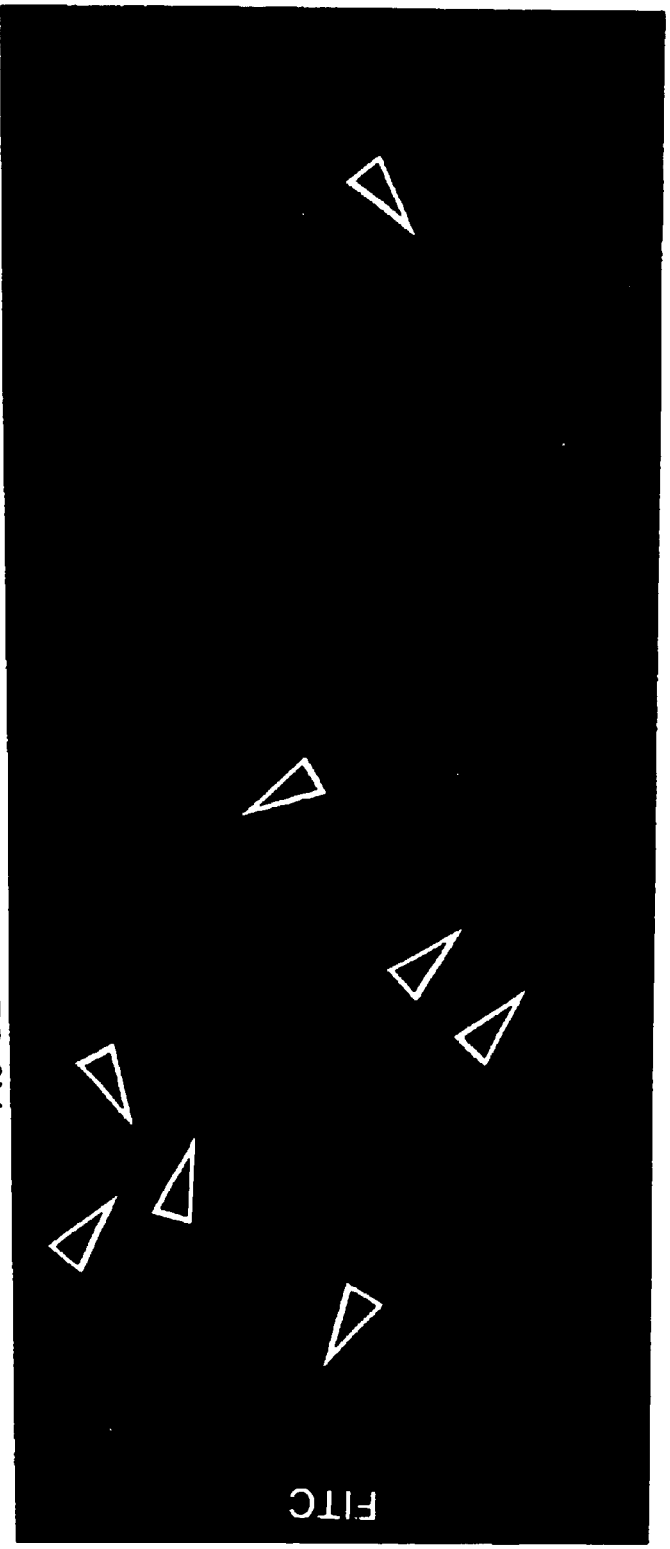

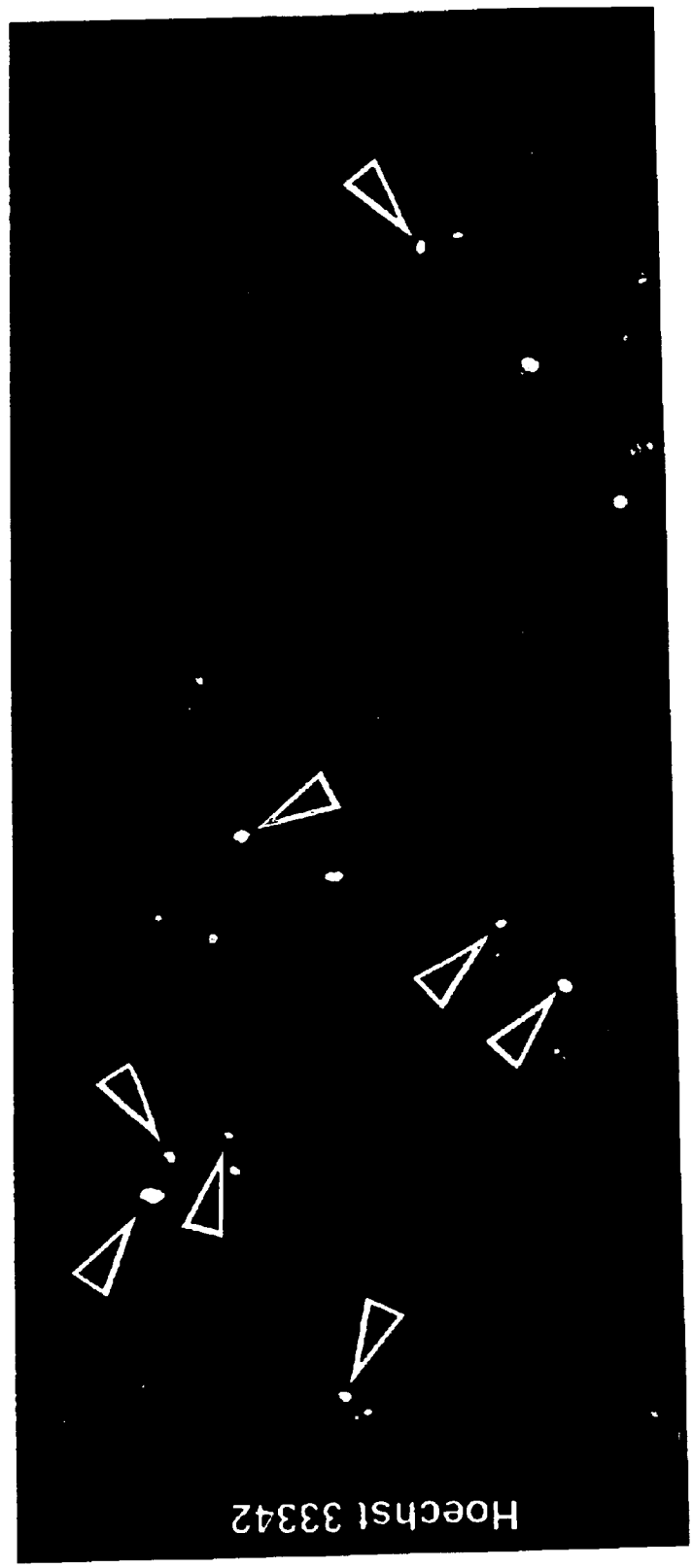

FIG. 7A

NGF R ceptor

```
  1 mgagatgram dgprllllll lgvslggake acptglyths gecckacnlg egvaqpcgan
 61 qtvcepclds vtfsdvvsat epckpctecv glqsmsapcv eaddavcrca ygyyqdettg
121 rceacrvcea gsglvfscqd kqmtvceecp dgtysdeanh vdpclpctvc edterqlrec
181 trwadaecee ipgrwitrst ppegsdstap stqepeappe qdliastvag vvttvmgssq
241 pvvtrgttdn lipvycsila avvvglvayi afkrwnsckq nkggansrpv nqtpppegek
301 lhsdsgisvd sqslhdqqph tqtasgqalk gdgglysslp pakreevekl lngsagdtwr
361 hlagelgyqp ehidsfthea cpvrallasw atqdsatlda llaalrriqr adlveslcse
421 statspv
```

FIG. 7B

CD4 Receptor

```
  1 mnrgvpfrhl llvlqlallp aatggkkvvl gkkgdtvelt ctasqkksiq fhwknsnqik
 61 ilgnqgsflt kgpsklndra dsrrslwdgg nfpliiknlk iedsdtyice vedqkeevql
121 lvfgltansd thllgqqslt ltlesppgss ltlesppgss psvqcrsprg kniggktls vsqlelqdsg
181 twtctvlqnq kkvefkidiv vlafqkassi vsvkrvtqdp klqmgkklpl hitlpqalpq yagsgnltla
241 qaerasssks witfdlknke vsvkrvtqdp klqmgkklpl hitlpqalpq yagsgnltla
301 leaktgklhq evnlvvmrat qlqknltcev wgptspkml slklenkeak vskrekavwv
361 lnpeagmwqc llsdsgqvll esnikvlptw stpvqpmali vlggvaglll figlgiffcv
421 rcrhrrrqae rmsqikrlls ekktcqcphr fqktcspi
```

FIG. 7C

| Species | C-terminal sequences of NGFR (p75) | Binding activity of FAP-1 |
|---|---|---|
| Human | fSESTATSPV-COOH | + |
| Rat | fSESTATSPV-COOH | + |
| Chicken | fSESTATSPV-COOH | + |

FIG. 7D

```
  1 mnsgvamkyg ndssaelsel hsaalaslkg divelnkrlq qtererdile kklakaqceq
 61 shlmrehedv qerttlryee ritelhsvia elnkkidrlq gttireedey selrselsqs
121 qhevnedsrs mdgdqtsvsi pengstmvta dmdncsdins elqrvitgle nvvcgrkkss
181 cslsvaevdr hieqlttase hcdlaiktve elgvlgrdl ypnlaeersr wekelagire
241 enesltamlc skeeelnrtk atmnaireer drlrrrvzel qtrlqsvqat gpsspgrlts
301 tnrplmpstg elatsssnd iptakiaarv klsktreess ssdrpvlgse lsslgvsssv
361 aehiahslqd csniqeifqt lyshgsaise skirefevet erlnsriehl ksqmdlltlt
421 leecksnaer msmlvgkyes natalrlalq yseqcieaye lllalaeseq slilgcfraa
481 gvgsspgdqs gdenitqmlk rabdcrktae naakalinki dgscggafav agcsvqpwes
541 lssnshtstt sstasscdte ftkedeqrlk dyiqqlmdr aavkltmlel esihidplsy
601 dvkprgdsqr ldlenavlmq elmamkeema elkaqlylla kekkalelkl streaqeqay
661 lvhiehlkse veeqkeqrmr sisstssgsk dkpgkecada aspalslael rttcsenela
721 aeftpairme kklkarvqel vsaleritks seirhqqsae fvmdlkrans nlvaayekak
781 kkhqmklkkl esqmmamver hetqvrmlkg rialleeens rphcnetsl
```

FIG. 7E

```
  1 madvfpgnds tasqdvanrf arkgalrqkn vhevkdhkfi arffkqptfc shctdfiwgf
 61 gkqgfgcqvc cfvvhkrche fvtfscpgad kgpdtdcprs khkfkihtyg sptfcdhcgs
121 llyglihqgm kedtcdmnvh kqcvlnvpsl cgmdhtekrg riylkaevad eklhvtvrda
181 knlipmdpcg lsdpyvkikl ipdpkmeskq ktktirstln pqwmesftfk lkpsdkdrrl
241 sveiwdwdrt trmdfmgsls fgvselmkmp asgwykling eegeyynvpl pegdeegnme
301 lrqkfekakl gpagnkvisp sedrkcpsnn ldrvkltdfn flmvlgkgsf gkvmladrkg
361 teelyaikil kkdvviqddd vectmvekrv lalldkppfl tqlhscfqtv drlyfvmeyv
421 nggdimybiq qvgkfkepqa vfyaaelsig lfflhkrgii yrdiklidnvm ldsaghikia
481 dfgmckehmn dgvttrtfcg tpdyiapeii ayqpygksvd wwaygvllye nlagqppfdg
541 ededelfqsi mehqvsypks iskeavsick glmtkhpakr lcgpegerd vrehaffrri
601 dweklenrel qppfkpkvcg kgaenfdkff trgppvltpp dqlvianidq sdfegfsyvn
661 pqfvhpllqT AI
```

FIG. 7F

```
  1 mdilceents lsttcnslmg lnddtrlysn dfnsgearts dafnwtvdse nrtalscegc
 61 lspsclslh lqekmwsall tavviltia gmlvimavs lekklgmatn yflmslaiad
121 mligflvmpv smtilygyr wplpskicav wlyldvlfst asimhlcais ldryvaiqmp
181 ihhsrfnsrt kaflkliavw tisvgismpl pvfglqddsk vfkegsclla ddnfvligef
241 vsffipltim vityfltiks lqkeaticvs digtraklas fsflpqesls sekifqrsih
301 repgsytgrr tmgsisneqk ackvlgivff lfvvmwcpff itrinavick escnedviga
361 linvfvwigy ssavmplvy tlfnktyrsa fsrylgcgyk enkkplqlil vntipalayk
421 ssqlqmgqkk nskqdaktcd ndcsmvalgk qhseeaskdn sdgvmekvgg_y
```

FIG. 7G

```
  1 malsyrvsei qstipehilq stivhvissn wsglqtesip eemkgiveeq gnklhwaall
 61 ilmvilptig gmtlvilavs lekklqvatn yflmelavad livglfvmpl alltimfeam
121 wplplvlcpa wlfldvlfst asimhlcals vdryiaikkp iganqynsra tafikitvvw
181 lisiglaipv pikgletdvd npnmiccvlt kerfgdfml- gslaafftpl aimivtyflt
241 ihalqkkayl vmnkpppqrlt witvstvfqr detpcsspek vamldgsrkd kalpnsgdet
301 lmrrtstigk ksvqtieneq raskvlgivf elfllmwcpf fitnitlvlc dscnqttlqm
361 lleifwigy vssgvmplvy tlfnktfrda fgryitcnyr atksvktlrk rsekiyfmp
421 maemskffkk hgirmgiapa myqspmrlrs stiqsesil idtllltene gdkteeqvmY
481 Y
```

FIG. 7H

```
   1 maaasydqli kqvealkmen snlrqeledn snhltklete asnmkevlkq lqgsiedeam
  61 assgqidlle rlkelnldss nfpgvklrsk mslrsygere gsvssrsgec spvpmgsfpr
 121 rgfvngsres tgyleeleke rsilladldk eekekdwyya qlqnltkrid slpltenfsl
 181 qtdmtrrqle yearqirvam eeqlgtcqdm ekraqrriar iqqiekdilr irqllqsqat
 241 eaerssqnkh etgshdaerq negqgvgein matsgngqgs ttrmdnetas vlssssthsa
 301 prrltshlgt kvemvyslls mlgthdkddm srtllamsss qdscismrqs gclplliqll
 361 hgndkdsvll gnsrgskear arasaalhni ihsqpddkrg rreirvlhll eqiraycetc
 421 wewqeahepg mdqdknpmpa pvehqicpav cvlmklsfde ehrhamnelg glqaiaellq
 481 vdcemygltn dhysitlrry agmaltnltf gdvankatlc smkgcmralv aqlkseseedl
 541 qqviasvlrn lswradvnsk ktlrevgsvk almecalevk kestlksvls alwnlsahct
 601 enkadicavd galaflvgtl tyrsqtntla iiesgggilr nvssliatne dhrqilrenn
 661 clqtllqhlk shsltivsna cgtlwnlsar npkdqealwd mgavsmlknl ihskhkmiam
 721 gsaaalrnlm anrpakykda nimspgsslp slhvrkqkal eaeldaqhls etfdnidnls
 781 pkashrskqr hkqslygdyv fdtnrhddnr sdnfntgnmt vlspylnttv lpsssssrgs
 841 ldssrsekdr slerergigl gnyhpatenp gtsskrglqi sttaqiakv meevsaihts
 901 qedrssgstt elhcvtdern alrrssaaht hsntynftks ensnrtcsmp yakleykrss
 961 ndslnsvsss dgygkrgqmk psiesysedd eskfcsygqy padlabkihs anhmddndge
1021 ldtpinyslk ysdeqlnsgr qspsqnerwa rpkhliedei kqseqrqsrn qsttypvyte
1081 stddkhlkfq phfgqqecvs pyrsrgangs etnrvgsnhg inqnvsqslc qeddyeddkp
1141 tnyserysee eqheeeerpt nysikyneek rhvdqpidys lkyatdipss qkqsfsfsks
1201 ssgqssekteh msssssentst pssnakrqnq lhpssaqsrs gqpqkaatck vssinqetiq
1261 tycvedtpic fsrcsslesl ssaedeigcn qttqeadsan tlqiaeikek igtrsaedgv
1321 sevpavsqhp rtkssrlqgs slssesarhk avefssgaks peksgaqtpk sppehyvqet
1381 plmfsrctsv ssldsfesrs lassvqsepc sgmvsgiisp sdlpdspgqt mppsrsktpp
1441 pppqtaqtkr evpknkapta ekresgpkqa avnaavqrvq vlpdadtllh fatestpdgf
1501 scssslsals ldepfiqkdv elrimppvqe ndngretese qpkesnenqe keaaktidse
1561 kdlldsdddd dieileecii samptksesrk akkpaqtask lpppvarkps qlpvykllps
1621 qnrlqpqkhv sftpgddmpr vycvegtpin fstatsledl tiesppnela agegvrggaq
1681 sgefekrdti ptegrstdea qggktssvti pelddnkaee gdilaecins ampkgkshkp
1741 frvkkimdqv qqasassesap nknqldgkkk kptspvkpip qnteyrtrvr knadsknnln
1801 aervfsdnkd skkqnlknns kdfndklpnn edrvrgsfaf dsphhytpie gtpycfsrnd
1861 slssldfddd dvdlsrekae lrkakenkes eakvtshtei tsnqqsankt qaiakqpinr
1921 gqpkpilqkq stfpqsskdi pdrgaatdek lqnfaientp vcfshnssls slsdidqenn
1981 nkenepiket eppdsqgeps kpqasgyapk sfhvedtpvc fsrnsslssl sidseddllq
2041 ecissampkk kkpsrlkgdn ekhsprnmgg ilgedltldl kdiqrpdseh glspdsenfd
2101 wkaiqegans iveslhqaaa aaclsrqass dsdsilslks gislgspfhl tpdqeekpft
2161 snkgprilkp gekstletkk ieseskgikg gkkvykslit gkvrsnseis gqmkqplqan
2221 mpsisrgrtm ihipgvrnss ssstspvskkg pplktpasks pseggtatts prgakpsvks
2281 elspvarqts qiggsskaps rsgsrdstps rpaqqplsrp iqspgrnsis pgrngisppn
2341 klsqlprtss petastkssg sgkmsytspg rqmsqqnltk qtglsknass iprsesaskg
2401 lnqmngnga nkkvelsrms stkssgsesd rserpvlvrq stfikeapsp tlrrkleesa
2461 efeslspssr pasptrsqaq tpvlspslpd mslsthssvq aggwrklppn lsptieyndg
2521 rpakrhdiar shsespsrlp inrsgtwkre hskhssslpr vstwrrtgss ssilsasses
2581 sekaksed k hvnsisgtkq skenqvsakg twrkikenef sptnsteqtv ssgatngaes
2641 ktliygmapa vsktedvwvr iedcpinnpr sgreptgntp pvidsvseka npnikdskdn
2701 qakqnvgngs vpmrtvglen rlnsfiqvda pdqkgteikp gqnnpvpvse tnsssivert
2761 pfsssssskh sspsgtvaar vtpfnynpsp rkssadstsa rpsqiptpvn nntkkrdskt
2821 dstessgtqs pkrhsgsylv tsv
```

COMPOUNDS THAT INHIBIT THE INTERACTION BETWEEN SIGNAL-TRANSDUCING PROTEINS AND THE GLGF (PDZ/DHR) DOMAIN AND USES THEREOF

The invention disclosed herein was made with Government support under Grant No. R01GM55147-01 from the National Institutes of Health of the United States Department of Health and Human Services. Accordingly, the U.S. Government has certain rights in this invention.

BACKGROUND

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Fas (APO-1/CD95) and its ligand have been identified as important signal-mediators of apoptosis (Itoh, et al. 1991) The structural organization of Fas (APO-1/CD95) has suggested that it is a member of the tumor necrosis factor receptor superfamily, which also includes the p75 nerve growth factor receptor (NGFR) (Johnson, et al. 1986), the T-cell-activation marker CD27 (Camerini, et al. 1991), the Hodgkin-lymphoma-associated antigen CD30 (Smith, et al. (1993), the human B cell antigen CD40 (Stamenkovic, et al. 1989), and T cell antigen OX40 (Mallett, et al. 1990). Genetic mutations of both Fas and its ligand have been associated with lymphoproliferative and autoimmune disorders in mice (Watanabe-Fukunaga, et al. 1992; Takahashi, et al. 1994).

Furthermore, alterations of Fas expression level have been thought to lead to the induction of apoptosis in T-cells infected with human immunodeficiency virus (HIV) (Westendorp, et al. 1995).

Several Fas-interacting signal transducing molecules, such as Fas-associated phosphatase-1 (FAP-1) (FIG. 1) (Sato, et al. 1995) FADD/MORT1/CAP-1/CAP-2 (Chinnaiyan, et al. 1995; Boldin, et al. 1995; Kischkel, et al. 1995) and RIP (Stanger, et al. 1995), have been identified using yeast two-hybrid and biochemical approaches. All but FAP-1 associate with the functional cell death domain of Fas and overexpression of FADD/MORT1 or RIP induces apoptosis in cells transfected with these proteins. In contrast, FAP-1 is the only protein that associates with the negative regulatory domain (C-terminal 15 amino acids) (Ito, et al. 1993) of Fas and that inhibits Fas-induced apoptosis.

FAP-1 (PTPN13) has several alternatively-spliced forms that are identical to PTP-BAS/hPTP1E/PTPL1, (Maekawa, et al. 1994; Banville, et al. 1994; Saras, et al. 1994) and contains a membrane-binding region similar to those found in the cytoskeleton-associated proteins, ezrin, (Gould et al. 1989) radixin (Funayama et al. 1991) moesin (Lankes, et al. 1991), neurofibromatosis type II gene product (NFII) (Rouleau, et al. 1993), and protein 4.1 (Conboy, et al. 1991), as well as in the PTPases PTPH1 (Yang, et al. 1991), PTP-MEG (Gu, et al. 1991), and PTPD1 (Vogel, et al. 1993). FAP-1 intriguingly contains six GLGF (PDZ/DHR) repeats that are thought to mediate intra- and inter-molecular interactions among protein domains. The third GLGF repeat of FAP-1 was first identified as a domain showing the specific interaction with the C-terminus of Fas receptor (Sato, et al. 1995). This suggests that the GLGF domain may play an important role in targeting proteins to the submembranous cytoskeleton and/or in regulating biochemical activity. GLGF repeats have been previously found in guanylate kinases, as well as in the rat post-synaptic density protein (PSD-95) (Cho, et al. 1992), which is a homolog of the Drosophila tumor suppressor protein, lethal-(1)-disc-large-1 [dlg-1] (Woods, et al 1991; Kitamura, et al. 1994). These repeats may mediate homo- and hetero-dimerization, which could potentially influence PTPase activity, binding to Fas, and/or interactions of FAP-1 with other signal transduction proteins. Recently, it has also been reported that the different PDZ domains of proteins interact with the C-terminus of ion channels and other proteins (FIG. 1) (TABLE 1) (Kornau, et al. 1995; Kim, et al. 1995; Matsumine, et al. 1996)

TABLE 1

Proteins that interact with PDZ domains.

| Protein | C-terminal sequence | Associated protein | Reference |
|---|---|---|---|
| Fas (APO-1/CD95) | SLV | FAP-1 | 2 |
| NMDA receptor NR2 subunit | SDV | PSD95 | 3 |
| Shaker-type K+ channel | TDV | PSD95 & DLG | 4 |
| APC | TEV | DLG | 5 |

SUMMARY OF THE INVENTION

This invention provides a composition capable of inhibiting specific binding between a signal-transducing protein and a cytoplasmic protein containing the amino acid sequence (G/S/A/E)-L-G-(F/I/L) (Sequence I.D. No.: 1). Further, the cytoplasmic protein may contain the amino acid sequence (K/R/Q)-$X_n$-(G/S/A/E)-L-G-(F/I/L) (Sequence I.D. No.: 2), wherein X represents any amino acid which is selected from the group comprising the twenty naturally occurring amino acids and n represents at least 2, but not more than 4. In a preferred embodiment, the amino acid sequence is SLGI (Sequence I.D. No.: 3). Further, the invention provides for a composition when the signal-transducing protein has at its carboxyl terminus the amino acid sequence (S/T)-X-(V/I/L) (Sequence I.D. No.: 4), wherein each—represents a peptide bond, each parenthesis encloses amino acids which are alternatives to one other, each slash within such parentheses separating the alternative amino acids, and the X represents any amino acid which is selected from the group comprising the twenty naturally occurring amino acids.

This invention also provides for a method of identifying a compound capable of inhibiting specific binding between a signal-transducing protein and a cytoplasmic protein containing the amino acid sequence (G/S/A/E)-L-G-(F/I/L) (SEQ ID NO: 1). Further this invention provides for a method of identifying a compound capable of inhibiting specific binding between a signal-transducing protein having at its carboxyl terminus the amino acid sequence (S/T)-X-(V/L/I) (SEQ ID NO: 4) and a cytoplasmic protein.

This invention also provides for a method inhibiting the proliferation of cancer cells, specifically, where the cancer cells are derived from organs comprising the colon, liver, breast, ovary, testis, lung, stomach, spleen, kidney, prostate, uterus, skin, head, thymus and neck, or the cells are derived from either T-cells or B-cells.

This invention also provides for a method of treating cancer in a subject in an amount of the composition of effective to result in apoptosis of the cells, specifically, where the cancer cells are derived from organs comprising the thymus, colon, liver, breast, ovary, testis, lung, stomach, spleen, kidney, prostate, uterus, skin, head and neck, or the cells are derived from either T-cells or B-cells.

This invention also provides for a method of inhibiting the proliferation of virally infected cells, specifically wherein the virally infected cells are infected with the Hepatitis B virus, Epstein-Barr virus, influenza virus, Papilloma virus, Adenovirus, Human T-cell lymphtropic virus, type 1 or HIV.

This invention also provides a pharmaceutical composition comprising compositions capable of inhibiting specific binding between a signal-transducing protein and a cytoplasmic protein.

This invention also provides a pharmaceutical composition comprising compounds identified to be capable of inhibiting specific binding between a signal-transducing protein and a cytoplasmic protein.

BRIEF DESCRIPTION OF THE FIGURES

As used herein, amino acid residues are abbreviated as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIGS. 2A, 2B, 2C and 2D. Mapping of the minimal region of the C-terminal of Has required for the binding to FAP-1. Numbers at right show each independent clone (FIGS. 2C and 2D).

2A. Strategy for screening of a random peptide library by the yeast two-hybrid system.

2B. Alignment of the C-terminal 15 amino acids of Fas between human (Sequence I.D. No.: 5), rat (Sequence I.D. No.: 6), and mouse (Sequence I.D. No.: 7).

2C. The results of screening a semi-random peptide library. Top row indicates the amino acids which were fixed based on the homology between human and rat. Dash lines show unchanged amino acids.

2D. The results of screening a random peptide library (Sequence I.D. No.: 8, Sequence I.D. No.: 9, Sequence I.D. No.: 10, Sequence I.D. No.: 11, Sequence I.D. No.: 12, Sequence I.D. No.: 13, Sequence I.D. No.: 14, Sequence I.D. No.: 15, Sequence I.D. No.: 16, Sequence I.D. No.: 17, respectively).

Figure 1:
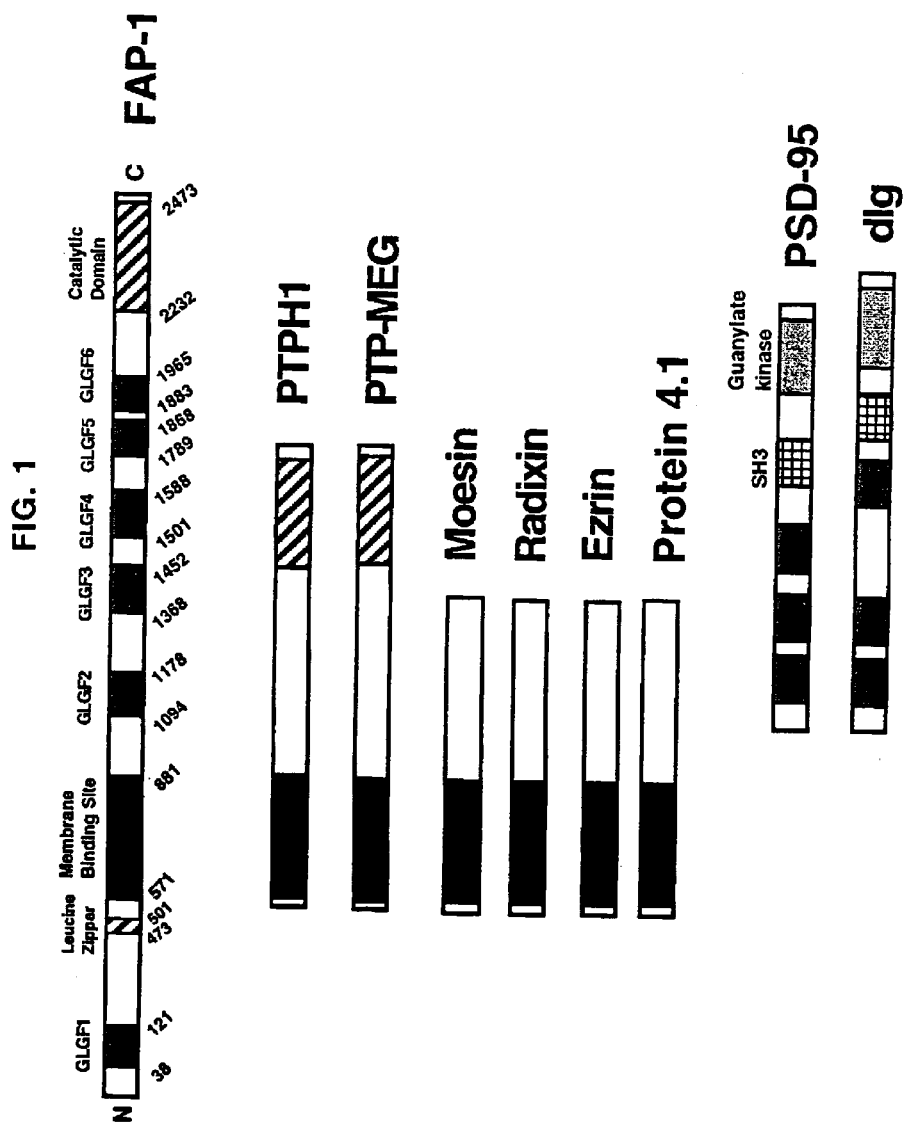
FIG. 1. Diagram of Fas-associated phosphatase-1 protein, showing the six GLGF (PDZ/DHR) domain repeats; comparison of similar membrane binding sites with other proteins and proteins that contain GLGF (PDZ/DHR) repeats.
Figure 3A:
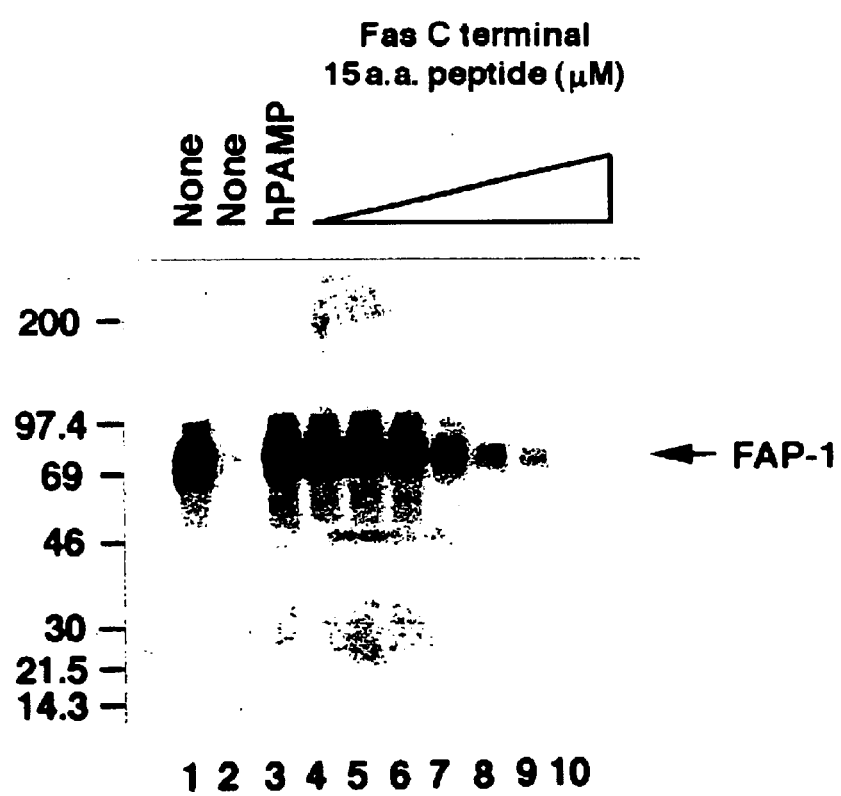
Figure 3B:
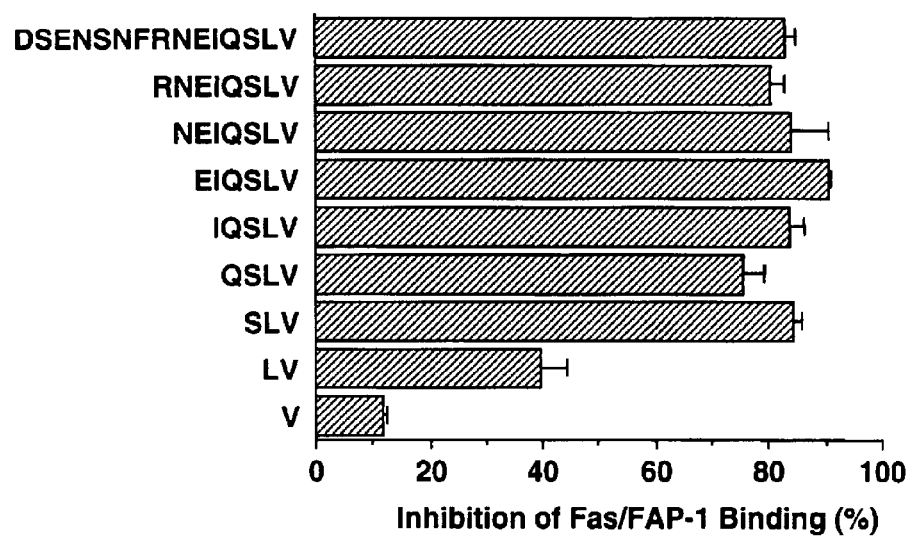

FIGS. 3A, 3B and 3C. Inhibition assay of Fas/FAP-1 binding vitro.

3A. Inhibition assay of Fas/FAP-1 binding using the C-terminal 15 amino acids of Fas. GST-Fas fusion protein (191–355) was used for in vitro binding assay (lane 1, 3–10). GST-Fas fusion protein (191–320) (lane 2) and 1 mM human PAMP (N-terminal 20 amino acids of proadrenomedullin, M.W. 2460.9) (lane 3) were used as negative controls. The concentrations of the C-terminal 15 amino acids added were 1 (lane 4), 3 (lane 5), 10 (lane 6), 30 (lane 7), 100 (lane 8), 300 (lane 9), and 1000 µM (lane 10).

3B. Inhibition assay of Fas/FAP-1 binding using the truncated peptides corresponding to the C-terminal 15 amino acids of Fas. All synthetic peptides were acetylated for this inhibition assay (Sequence I.D. No.: 4, Sequence I.D. No.: 18, Sequence I.D. No.: 19, Sequence I.D. No.: 20, Sequence ID. No.: 21, Sequence I.D. No.: 22, Sequence I.D. No.: 23, respectively).

3C Inhibitory effect of Fas/FAP-1 binding using the scanned tripeptides.

FIGS. 4A, 4B, 4C and 4D.

4A. Interaction of the C-terminal 3 amino acids of Fas with FAP-1 in yeast.

4B. Interaction of the C-terminal 3 amino acids of Fas with FAP-1 in vitro.

4C. Immuno-precipitation of native Fas with GST-FAP-1.

4D. Inhibition of Fas/FAP-1 binding with Ac-SLV or Ac-SLY.

FIGS. 5A, 5B, 5C, 5D, 5E and 5F. Microinjection of Ac-SLV into the DLD-1 cell line. Triangles identify the cells both that were microinjected with Ac-SLV and that condensed chromatin identified. On the other hand, only one cell of the area appeared apoptotic when microinjected with Ac-SLY.

5A. Representative examples of the cells microinjected with Ac-SLV in the presence of 500 ng/ml CH11 are shown in phase contrast.

5B. Representative examples of the cells microinjected with AC-SLY in the presence of 500 ng/ml CH11 are shown in phase contrast.

5C. Representative examples of the cells microinjected with Ac-SLV in the presence of 500 ng/ml CH11 are shown stained with FITC.

5D. Representative examples of the cells microinjected with AC-SLY in the presence of 500 ng/ml CH11 are shown stained with FITC.

5E. Representative examples of the cells microinjected with Ac-SLV in the presence of 500 ng/ml CH11 are shown with fluorescent DNA staining with Hoechst 33342.

5F. Representative examples of the cells microinjected with AC-SLY in the presence of 500 ng/ml CH11 are shown in fluorescent DNA staining with Hoechst 33342.

Figure 6:
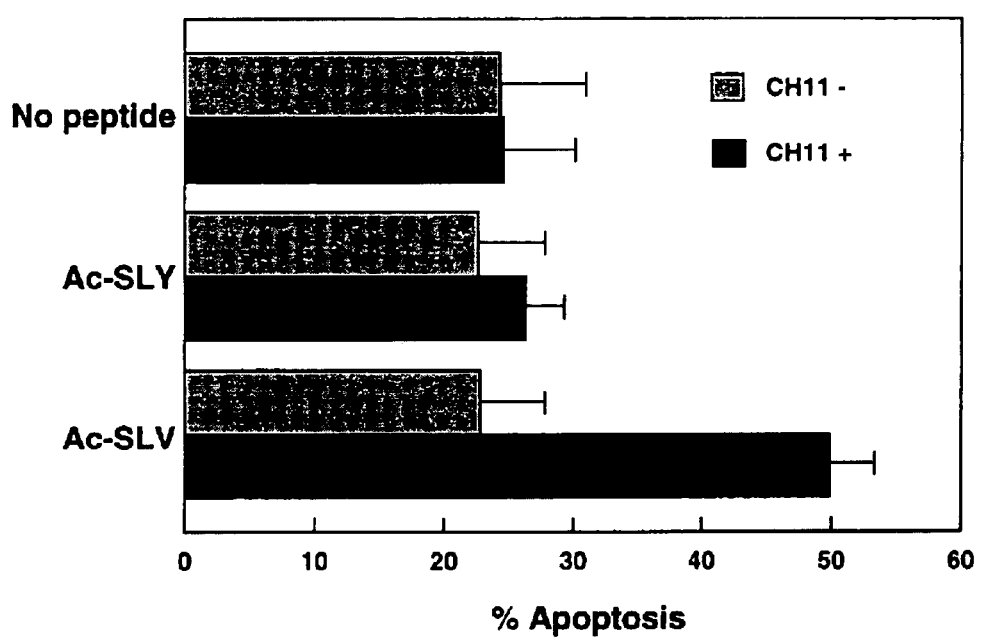

FIG. 6. Quantitation of apoptosis in microinjected DLD-1 cells.

FIGS. 7A, 7B, 7C, 7D, 7E, 7F, 7G, and 7H.

7A. Amino acid sequence of human nerve growth factor receptor (Sequence I.D. No.: 24).

7B. Amino acid sequence of human CD4 receptor (Sequence I.D. No. 25).

7C. The interaction of Fas-associated phosphatase-1 to the C-terminal of nerve growth factor receptor (NGFR) (p75).

7D. Amino acid sequence of human colorectal mutant cancer protein (Sequence I.D. No.: 26).

7E. Amino acid sequence of protein kinase C, alpha type (SEQ ID NO: 27).

7F. Amino acid sequence of serotonin 2A receptor (SEQ ID NO: 28).

7G. Amino acid sequence of serotonin 2B receptor (SEQ ID NO: 29).

7H. Amino acid sequence of adenomatosis polyposis *coli* protein (SEQ ID NO: 30).

DETAILED DESCRIPTION OF THE INVENTION

As used herein, amino acid residues are abbreviated as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

In order to facilitate an understanding of the material which follows, certain frequently occurring methods and/or terms are best described in Sambrook, et al., 1989.

The present invention provides for a composition capable of inhibiting specific binding between a signal-transducing protein and a cytoplasmic protein containing the amino acid sequence (G/S/A/E)-L-G-(F/I/L) (SEQ ID NO: 1), wherein each—represents a peptide bond, each parenthesis encloses amino acids which are alternatives to one other, and each slash within such parentheses separating the alternative amino acids. Further, the cytoplasmic protein may contain the amino acid sequence (K/R/Q)-X$_n$-(G/S/A/E)-L-G-(F/I/L) (SEQ ID NO: 2), wherein X represents any amino acid which is selected from the group comprising the twenty naturally occurring amino acids and n represents at least 2, but not more than 4. Specifically, in a preferred embodiment, the cytoplasmic protein contains the amino acid sequence SLGI (SEQ ID NO: 3).

The amino acid sequence (K/R/Q)-X$_n$-(G/S/A/E)-L-G-(F/I/L) (SEQ ID NO: 2) is also well-known in the art as "GLGF (PDZ/DHR) amino acid domain." As used herein, "GLGF (PDZ/DHR) amino acid domain" means the amino acid sequence (K/R/Q)-X$_n$-(G/S/A/E)-L-G-(F/I/L) (SEQ ID NO: 2).

In a preferred embodiment, the signal-transducing protein has at its carboxyl terminus the amino acid sequence (S/T)-X-(V/I/L) (SEQ ID NO: 4), wherein each—represents a peptide bond, each parenthesis encloses amino acids which are alternatives to one other, each slash within such parentheses separating the alternative amino acids, and the X represents any amino acid which is selected from the group comprising the twenty naturally occurring amino acids.

The compositions of the subject invention may be, but not limited to, antibodies, inorganic compounds, organic compounds, peptides, peptidomimetic compounds, polypeptides or proteins, fragments or derivatives which share some or all properties, e.g. fusion proteins. The composition may be naturally occurring and obtained by purification, or may be non-naturally occurring and obtained by synthesis.

Specifically, the composition may be a peptide containing the sequence (S/T)-X-(V/I/L)-COOH(SEQ ID NO: 4), wherein each—represents a peptide bond, each parenthesis encloses amino acids which are alternatives to one other, each slash within such parentheses separating the alternative amino acids, the X represents any amino acid which is selected from the group comprising the twenty naturally occurring amino acids. In preferred embodiments, the peptide contains one of the following sequences: DSENSNFRNEIQSLV(SEQ ID NO: 23), RNEIQSLV (SEQ ID NO: 22), NEIQSLV (SEQ ID NO: 21), EIQSLV (SEQ ID NO: 20), IQSLV (SEQ ID NO: 19), QSLV (SEQ ID NO: 18), SLV, IPPDSEDGNEEQSLV (SEQ ID NO: 17), DSEMYNFRSQLASVV (SEQ ID NO: 16), IDLASEFLFLSNSFL (SEQ ID NO: 15), PPTCSQANSGRISTL (SEQ ID NO: 14), SDSNMNMNELSEV (SEQ ID NO: 13), QNFRTYIVSFV (SEQ ID NO: 12), RETIESTV (SEQ ID NO: 11), RGFISSLV (SEQ ID NO: 10), TIQSVI (SEQ ID NO: 9), ESLV (SEQ ID NO: 8). A further preferred embodiment would be an organic compound which has the sequence Ac-SLV-COOH, wherein the Ac represents an aceytl and each—represents a peptide bond.

An example of the subject invention is provided infra. Acetylated peptides may be automatically synthesized on an Advanced ChemTech ACT357 using previously published procedures by analogy. Wang resin was used for each run and N$^\alpha$-Fmoc protection was used for all amino acids, and then 20% piperidine/DMF and coupling was completed using DIC/HOBt and subsequently HBTU/DIEA. After the last amino acid was coupled, the growing peptide on the resin was acetylated with Ac$_2$O/DMF. The acetylated peptide was purified by HPLC and characterized by FAB-MS and $^1$H-NMR.

Further, one skilled in the art would know how to construct derivatives of the above-described synthetic peptides coupled to non-acetyl groups, such as amines.

This invention also provides for a composition capable of inhibiting specific binding between a signal-transducing protein having at its carboxyl terminus the amino acid sequence (S/T)-X-(V/I/L) (SEQ ID NO: 4), wherein each—represents a peptide bond, each parenthesis encloses amino acids which are alternatives to one other, each slash within such parentheses separating the alternative amino acids, the X represents any amino acid which is selected from the group comprising the twenty naturally occurring amino acids, and a cytoplasmic protein.

The compositions of the subject invention includes antibodies, inorganic compounds, organic compounds, peptides, peptidomimetic compounds, polypeptides or proteins, fragments or derivatives which share some or all properties, e.g. fusion proteins.

This invention also provides a method of identifying a compound capable of inhibiting specific binding between a signal-transducing protein and a cytoplasmic protein containing the amino acid sequence (G/S/A/E)-L-G-(F/I/L) (SEQ ID NO: 1), wherein each—represents a peptide bond, each parenthesis encloses amino acids which are alternatives to one other, each slash within such parentheses separating the alternative amino acids, which comprises (a) contacting the cytoplasmic protein bound to the signal-transducing protein with a plurality of compounds under conditions permitting binding between a known compound previously shown to be able to displace the signal-transducing protein bound to the cytoplasmic protein and the bound cytoplasmic protein to form a complex; and (b) detecting the displaced signal-transducing protein or the complex formed in step (a) wherein the displacement indicates that the compound is capable of inhibiting specific binding between the signal-transducing protein and the cytoplasmic protein.

The inhibition of the specific binding between the signal-transducing protein and the cytoplasmic protein may affect the transcription activity of a reporter gene.

Further, in step (b), the displaced cytoplasmic protein or the complex is detected by comparing the transcription activity of a reporter gene before and after the contacting with the compound in step (a), where a change of the activity indicates that the specific binding between the signal-transducing protein and the cytoplasmic protein is inhibited and the signal-transducing protein is displaced.

As used herein, the "transcription activity of a reporter gene" means that the expression level of the reporter gene will be altered from the level observed when the signal-transducing protein and the cytoplasmic protein are bound. One can also identify the compound by detecting other biological functions dependent on the binding between the signal-transducing protein and the cytoplasmic protein. Examples of reporter genes are numerous and well-known in the art, including, but not limited to, histidine resistant genes, ampicillin resistant genes, β-galactosidase gene.

Further the cytoplasmic protein may be bound to a solid support. Also the compound may be bound to a solid support and comprises an antibody, an inorganic compound, an organic compound, a peptide, a peptidomimetic compound, a polypeptide or a protein.

An example of the method is provided infra. One can identify a compound capable of inhibiting specific binding between the signal-transducing protein and the cytoplasmic protein using direct methods of detection such as immunoprecipitation of the cytoplasmic protein and the compound bound to a detectable marker. Further, one could use indirect methods of detection that would detect the increase or decrease in levels of gene expression. As discussed infra, one could construct synthetic peptides fused to a LexA DNA binding domain. These constructs would be transformed into the L40-strain with an appropriate cell line having an appropriate reporter gene. One could then detect whether inhibition had occurred by detecting the levels of expression of the reporter gene. In order to detect the expression levels of the reporter gene, one skilled in the art could employ a variety of well-known methods, e.g. two-hybrid systems in yeast, mammals or other cells.

Further, the contacting of step (a) may be in vitro, in vivo, and specifically in an appropriate cell, e.g. yeast cell or mammalian cell. Examples of mammalian cells include, but not limited to, the mouse fibroblast cell NIH 3T3, CHO cells, HeLa cells, Ltk⁻ cells, Cos cells, etc.

Other suitable cells include, but are not limited to, prokaryotic or eukaryotic cells, e.g. bacterial cells (including gram positive cells), fungal cells, insect cells, and other animals cells.

Further, the signal-transducing protein may be a cell surface receptor, signal transducer protein, or a tumor suppressor protein. Specifically, the cell surface protein is the Fas receptor and may be expressed in cells derived from organs including, but not limited to, thymus, liver, kidney, colon, ovary, breast, testis, spleen, lung, stomach, prostate, uterus, skin, head, and neck, or expressed in cells comprising T-cells and B-cells. In a preferred embodiment, the T-cells are Jurkat T-cells.

Further, the cell-surface receptor may be a CD4 receptor, p75 receptor, serotonin 2A receptor, or serotonin 2B receptor.

Further, the signal transducer protein may be Protein Kinase-C-α-type.

Further, the tumor suppressor protein may be a adenomatosis polyposis coli tumor suppressor protein or colorectal mutant cancer protein.

Further, the cytoplasmic protein contains the amino acid sequence SLGI(SEQ ID NO: 3), specifically Fas-associated phosphatase-1.

This invention also provides a method of identifying a compound capable of inhibiting specific binding between a signal-transducing protein having at its carboxyl terminus the amino acid sequence (S/T)-X-(V/I/L) (SEQ ID NO: 4), wherein each—represents a peptide bond, each parenthesis encloses amino acids which are alternatives to one other, each slash within such parentheses separating the alternative amino acids, the X represents any amino acid which is selected from the group comprising the twenty naturally occurring amino acids, and a cytoplasmic protein which comprises (a) contacting the signal-transducing protein bound to the cytoplasmic protein with a plurality of compounds under conditions permitting binding between a known compound previously shown to be able to displace the cytoplasmic protein bound to the signal-transducing protein and bound signal-transducing protein to form a complex; and (b) detecting the displaced cytoplasmic protein or the complex of step (a), wherein the displacement indicates that the compound is capable of inhibiting specific binding between the signal-transducing protein and the cytoplasmic protein. The inhibition of the specific binding between the signal-transducing protein and the cytoplasmic protein affects the transcription activity of a reporter gene. Further, in step (b), the displaced signal-transducing protein or the complex is detected by comparing the transcription activity of a reporter gene before and after the contacting with the compound in step (a), where a change of the activity indicates that the specific binding between the signal-transducing protein and the cytoplasmic protein is inhibited and the cytoplasmic protein is displaced.

Further, in step (b), the displaced cytoplasmic protein or the complex is detected by comparing the transcription activity of a reporter gene before and after the contacting with the compound in step (a), where a change of the activity indicates that the specific binding between the signal-transducing protein and the cytoplasmic protein is inhibited and the signal-transducing protein is displaced.

As used herein, the "transcription activity of a reporter gene" means that the expression level of the reporter gene will be altered from the level observed when the signal-transducing protein and the cytoplasmic protein are bound. One can also identify the compound by detecting other biological functions dependent on the binding between the signal-transducing protein and the cytoplasmic protein. Examples of reporter genes are numerous and well-known in the art, including, but not limited to, histidine resistant genes, ampicillin resistant genes, β-galactosidase gene.

Further, the cytoplasmic protein may be bound to a solid support or the compound may be bound to a solid support, comprises an antibody, an inorganic compound, an organic compound, a peptide, a peptidomimetic compound, a polypeptide or a protein.

An example of the method is provided infra. One could identify a compound capable of inhibiting specific binding between the signal-transducing protein and the cytoplasmic protein using direct methods of detection such as immunoprecipitation of the cytoplasmic protein and the compound bound with a detectable marker. Further, one could use indirect methods of detection that would detect the increase or decrease in levels of gene expression. As discussed infra, one could construct synthetic peptides fused to a LexA DNA binding domain. These constructs would be transformed into L40-strain with an appropriate cell line having a reporter gene. One could then detect whether inhibition had occurred by detecting the levels of the reporter gene. Different methods are also well known in the art, such as employing a yeast two-hybrid system to detect the expression of a reporter gene.

Further the contacting of step (a) can be in vitro or in vivo, specifically in a yeast cell or a mammalian cell. Examples of mammalian cells include, but not limited to, the mouse fibroblast cell NIH 3T3, CHO cells, HeLa cells, Ltk⁻ cells, Cos cells, etc.

Other suitable cells include, but are not limited to, prokaryotic or eukaryotic cells, e.g. bacterial cells (including gram positive cells), fungal cells, insect cells, and other animals cells.

Further, the signal-transducing protein is a cell surface receptor, signal transducer protein, or a tumor suppressor protein. Specifically, the cell surface protein is the Fas receptor and is expressed in cells derived from organs comprising thymus, liver, kidney, colon, ovary, breast, testis, spleen, stomach, prostate, uterus, skin, head and neck, or expressed in cells comprising T-cells and B-cells. In a preferred embodiment, the T-cells are Jurkat T-cells.

Further, the cell-surface receptor may be a CD4 receptor, p75 receptor, serotonin 2A receptor, or serotonin 2B receptor.

Further, the signal transducer protein may be Protein Kinase-C-α-type.

Further, the tumor suppressor protein may be a adenomatosis polyposis coli tumor suppressor protein or colorectal mutant cancer protein.

Further, the cytoplasmic protein contains the amino acid sequence SLGI, specifically Fas-associated phosphatase-1.

This invention also provides a method of inhibiting the proliferation of cancer cells comprising the above-described composition, specifically, wherein the cancer cells are derived from organs including, but not limited to, thymus, liver, kidney, colon, ovary, breast, testis, spleen, stomach, prostate, uterus, skin, head and neck, or wherein the cancer cells are derived from cells comprising T-cells and B-cells.

This invention also provides a method of inhibiting the proliferation of cancer cells comprising the compound identified by the above-described method, wherein the cancer cells are derived from organs including, but not limited to, thymus, liver, kidney, colon, ovary, breast, testis, spleen, stomach, prostate, uterus, skin, head and neck, or wherein the cancer cells are derived from cells comprising T-cells and B-cells.

The invention also provides a method of treating cancer in a subject which comprises introducing to the subject's cancerous cells an amount of the above-described composition effective to result in apoptosis of the cells, wherein the cancer cells are derived from organs including, but not limited to, thymus, liver, kidney, colon, ovary, breast, testis, spleen, stomach, prostate, uterus, skin, head and neck, or wherein the cancer cells are derived from cells comprising T-cells and B-cells.

As used herein "apoptosis" means programmed cell death of the cell. The mechanisms and effects of programmed cell death differs from cell lysis. Some observable effects of apoptosis are: DNA fragmentation and disintegration into small membrane-bound fragments called apoptotic bodies.

Means of detecting whether the composition has been effective to result in apoptosis of the cells are well-known in the art. One means is by assessing the morphological change of chromatin using either phase contrast or fluorescence microscopy.

The invention also provides for a method of inhibiting the proliferation of virally infected cells comprising the above-described composition or the compound identified by the above-described, wherein the virally infected cells comprise Hepatitis B virus, Epstein-Barr virus, influenza virus, Papilloma virus, Adeno virus, Human T-cell lymphtropic virus, type 1 or HIV.

The invention also provides a method of treating a virally-infected subject which comprises introducing to the subject's virally-infected cells the above-described composition effective to result in apoptosis of the cells or the compound identified by the above-described method effective to result in apoptosis of the cells, wherein the virally infected cells comprise the Hepatitis B virus, Epstein-Barr virus, influenza virus, Papilloma virus, Adeno virus, Human T-cell lymphtropic virus, type 1 or HIV.

Means of detecting whether the composition has been effective to result in apoptosis of the cells are well-known in the art. One means is by assessing the morphological change of chromatin using either phase contrast or fluorescence microscopy.

This invention also provides for a pharmaceutical composition comprising the above-described composition of in an effective amount and a pharmaceutically acceptable carrier.

This invention also provides for a pharmaceutical composition comprising the compound identified by the above-described method of in an effective amount and a pharmaceutically acceptable carrier.

This invention further provides a composition capable of specifically binding a signal-transducing protein having at its carboxyl terminus the amino acid sequence (S/T)-X-(V/L/I) (SEQ ID NO: 4), wherein each—represents a peptide bond, each parenthesis encloses amino acids which are alternatives to one other, each slash within such parentheses separating the alternative amino acids, and the X represents any amino acid which is selected from the group comprising the twenty naturally occurring amino acids. The composition may contain the amino acid sequence (G/S/A/E)-L-G-(P/I/L) (SEQ ID NO: 1), wherein each—represents a peptide bond, each parenthesis encloses amino acids which are alternatives to one other, and each slash within such parentheses separating the alternative amino acids. In a preferred embodiment, the composition contains the amino acid sequence (K/R/Q)-$X_n$-(G/S/A/E)-L-G-(F/I/L) (SEQ ID NO: 2), wherein X represents any amino acid which is selected from the group comprising the twenty naturally occurring amino acids and n represents at least 2, but not more than 4. In another preferred embodiment, the composition contains the amino acid sequence SLGI(SEO ID NO: 3).

This invention further provides a method for identifying compounds capable of binding to a signal-transducing protein having at its carboxyl terminus the amino acid sequence (S/T)-X-(V/L/I) (SEQ ID NO: 4), wherein each—represents a peptide bond, each parenthesis encloses amino acids which are alternatives to one other, each slash within such parentheses separating the alternative amino acids, the X represents any amino acid which is selected from the group comprising the twenty naturally occurring amino acids, which comprises (a) contacting the signal-transducing protein with a plurality of compounds under conditions permitting binding between a known compound previously shown to be able to bind to the signal-transducing protein to form a complex; and (b) detecting the complex formed in step (a) so as to identify a compound capable of binding to the signal-transducing protein. Specifically, the identified compound contains the amino acid sequence (G/S/A/E)-L-G-(F/I/L) (SEQ ID NO: 1). In a further preferred embodiment, the identified compound contains the amino acid sequence SLGI (SEQ ID NO: 3).

Further, in the above-described method, the signal-transducing protein may be bound to a solid support. Also, the compound may be bound to a solid support, and may comprise an antibody, an inorganic compound, an organic compound, a peptide, a peptidomimetic compound, a polypeptide or a protein.

Further, the signal-transducing protein may be a cell-surface receptor or a signal transducer. Specifically, the signal-transducing protein may be the Fas receptor, CD4 receptor, p75 receptor, serotonin 2A receptor, serotonin 2B receptor, or protein kinase-C-α-type.

This invention also provides a method of restoring negative regulation of apoptosis in a cell comprising the above-described composition or a compound identified by the above-described method.

As used herein restoring negative regulation of apoptosis means enabling the cell from proceeding onto programmed cell death.

For example, cells that have functional Fas receptors and Fas-associated phosphatase 1 do not proceed onto programmed cell death or apoptosis due to the negative regulation of Fas by the phosphatase. However, if Fas-associated phosphatase 1 is unable to bind to the carboxyl terminus of the Fas receptor ((S/T)-X-(V/L/I) (SEQ ID NO: 4) region)), e.g. mutation or deletion of at least one of the amino acids in the amino acid sequence (G/S/A/E)-L-G-(F/I/L) (SEQ ID NO: 1), the cell will proceed to apoptosis. By introducing a compound capable of binding to the carboxyl terminus of the Fas receptor, one could mimic the effects of a functional phosphatase and thus restore the negative regulation of apoptosis.

This invention also provides a method of preventing apoptosis in a cell comprising the above-described composition or a compound identified by the above-described method.

This invention also provides a means of treating pathogenic conditions caused by apoptosis of relevant cells comprising the above-described composition or the compound identified by the above-described method.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Methods and Materials

1. Screening a semi-random and random peptide library.

To create numerous mutations in a restricted DNA sequence, PCR mutagenesis with degenerate oligonucleotides was employed according to a protocol described elsewhere (Hill, et al. 1987). Based on the homology between human and rat, two palindromic sequences were designed for construction of semi-random library. The two primers used were 5'-CGGAATTCNNNNNNNNNNAACAGCNNNNNNNNNNAATGAANNNCAAAGTCTGNNNTGAGGATCC TCA-3' (SEQ ID NO: 31) and 5'-CGGAATTCGACTCAGAANNNNNNAACTTCAGANNNNNNATCNNNNNNNNNGTCTGAGGATCC TCA-3' (SEQ ID NO: 32). Briefly, the two primers (each 200 pmol), purified by HPLC, were annealed at 70° C. for 5 minutes and cooled at 23° C. for 60 minutes. A Klenow fragment (5 U) was used for filling in with a dNTP mix (final concentration, 1 mM per each dNTP) at 23° C. for 60 minutes. The reaction was stopped with 1 $\mu$l of 0.5 M EDTA and the DNA was purified with ethanol precipitation. The resulting double-stranded DNA was digested with EcoRI and BamHI and re-purified by electrophoresis on non-denaturing polyacrylamide gels. The double-strand oligonucleotides were then ligated into the EcoRI-BamHI sites of the pBTM116 plasmid. The ligation mixtures were electroporated into the *E. coil* XL1-Blue MRF' (Stratagene) for the plasmid library. The large scale transformation was carried out as previously reported. The plasmid library was transformed into L40-strain cells (MATa, trp1, leu2, his3, ade2, LYS2: (lexAop)$^4$-HIS3, URA3: (lexAop)$^8$-lacZ) carrying the plasmid pVP16–31 containing a FAP-1 cDNA (Sato, et al. 1995). Clones that formed on histidine-deficient medium (His$^+$) were transferred to plates containing 40 $\mu$g/ml X-gal to test for a blue reaction product ($\beta$-gal$^+$) in plate and filter assays. The clones selected by His$^+$ and $\beta$-gal$^+$ assay were tested for further analysis. The palindromic oligonucleotide, 5'-CGGAATTC-(NNN)$_{4-15}$-TGAGGATCCTCA-3' (Seq. I.D. No. 33), was used for the construction of the random peptide library.

2. Synthesis of peptides

Peptides were automatically synthesized on an Advanced ChemTech ACT357 by analogy to published procedures (Schnorrenberg and Gerhardt, 1989). Wang resin (C.2–0.3 mmole scale) was used for each run and N$^\alpha$-Fmoc protection was employed for all amino acids. Deprotection was achieved by treatment with 20% piperidine/DMF and coupling was completed using DIC/HOBt and subsequent HBTU/DIEA. After the last amino acid was coupled, the growing peptide on the resin was acetylated with $Ac_2O$/DMF. The peptide was cleaved from the resin with concomitant removal of all protecting groups by treating with TFA. The acetylated peptide was purified by HPLC and characterized by FAB-MS and $^1$H-NMR.

3. Inhibition asssay of Fas/FAP-1 binding using the C-terminal 15 amino acids of Fas.

HFAP-10 cDNA (Sato, et al. 1995) subcloned into the Bluescript vector pSK-II (Stratagene) was in vitro-translated from an internal methionine codon in the presence of $^{35}$S-L-methionine using a coupled in vitro transcription/translation system (Promega, TNT lysate) and T7 RNA polymerase. The resulting $^{35}$S-labeled protein was incubated with GST-Fas fusion proteins that had been immobilized on GST-Sepharose 4B affinity beads (Pharmacia) in a buffer containing 150 mM NaCl, 50 mM Tris [pH 8.0], 5 mM DTT, 2 mM EDTA, 0.1% NP-40, 1 mM PMSF, 50 $\mu$g/ml leupeptin, 1 mM Benzamidine, and 7 $\mu$g/ml pepstatin for 16 hours at 4° C. After washing vigorously 4 times in the same buffer, associated proteins were recovered with the glutathione-Sepharose beads by centrifugation, eluted into boiling Laemmli buffer, and analyzed by SDS-PAGE and fluorography.

4. Inhibition assay of terminal 15 amino acids of Fas and inhibitory effect of Fas/FAP-1 binding using diverse tripeptides.

In vitro-translated [$^{35}$S]HFAP-1 was purified with a NAP-5 column (Pharmacia) and incubated with 3 $\mu$M of GST-fusion proteins for 16 hours at 4° C. After washing 4 times in the binding buffer, radioactivity incorporation was determined in a b counter. The percentage of binding inhibition was calculated as follows: percent inhibition=[radioactivity incorporation using GST-Fas (191–335) with peptides–radioactivity incorporation using GST-Fas (191–320) with peptides]/[radioactivity incorporation using GST-Fas (191–335) without peptides–radioactivity incorporation using GST-Fas (191–320) without peptides]. n=3.

5. Interaction of the C-terminal 3 amino acids of Fas with FAP-1 in yeast and in vitro.

The bait plasmids, pBTM116 (LexA)-SLV, -PLV, -SLY, and -SLA, were constructed and transformed into L40-strain with pVP16-FAP-1 or -ras. Six independent clones from each transformants were picked up for the analysis of growth on histidine-deficient medium. GST-Fas, -SLV, and PLV were purified with GST-Sepharose 4B affinity beads (Pharmacia). The methods for in vitro binding are described above.

6. Immuno-precipitation of native Fas with GST-FAP-1 and inhibition of Fas/FAP-1 binding with Ac-SLV.

GST-fusion proteins with or without FAP-1 were incubated with cell extracts from Jurkat T-cells expressing Fas. The bound Fas was detected by Western analysis using anti-Fas monoclonal antibody (F22120, Transduction Laboratories). The tripeptides, Ac-SLV and Ac-SLY were used for the inhibition assay of Pas/FAP-1 binding.

7. Microinjection of Ac-SLV into the DLD-1 cell line.

DLD-1 human colon cancer cells were cultured in RPMI 1640 medium containing 10% FCS. For microinjection, cells were plated on CELLocate (Eppendorf) at $1 \times 10^5$ cells/2 ml in a 35 mm plastic culture dish and grown for 1 day. Just before microinjection, Fas monoclonal antibodies CH11 (MBL International) was added at the concentration of 500 ng/ml. All microinjection experiments were performed using an automatic microinjection system (Eppendorf transjector 5246, micro-manipulator 5171 and Femtotips) (Pantel, et al. 1995). Synthetic tripeptides were suspended in 0.1% (w/v) FITC-Dextran (Sigma)/K-PBS at the concentration of 100 mM. The samples were microinjected into the cytoplasmic region of DLD-1 cells. Sixteen to 20 hours postinjection, the cells were washed with PBS and stained with 10 $\mu$g/ml Hoechst 33342 in PBS. After incubation at 37° C. for 30 minutes, the cells were photographed and the cells showing condensed chromatin were counted as apoptotic.

8. Quantitation of apoptosis in microinjected DLD-1 cells.

For each experiment, 25–100 cells were microinjected. Apoptosis of microinjected cells was determined by assessing morphological changes of chromatin using phase contrast and fluorescence microscopy (Wang, et al., 1995; McGahon, et al., 1995). The data are means +/– S.D. for two or three independent determinations.

Discussion

In order to identify the minimal peptide stretch in the C-terminal region of the Fas receptor necessary for FAP-1 binding, an in vitro inhibition assay of Fas/FAP-1 binding was used using a series of synthetic peptides as well as yeast two-hybrid system peptide libraries (FIG. 2A). First, semi-random libraries (based on the homology between human and rat Fas) (FIGS. 2B and 2C) of 15 amino acids fused to a LexA DNA binding domain were constructed and co-transformed into yeast strain L40 with pVP16–31 (Sato, et al. 1995) that was originally isolated as FAP-l. After the selection of 200 His$^+$ colonies from an initial screen of $5.0 \times 10^5$ (Johnson, et al. 1986) transformants, 100 colonies that were β-galactosidase positive were picked for further analysis. Sequence analysis of the library plasmids encoding the C-terminal 15 amino acids revealed that all of the C-termini were either valine, leucine or isoleucine residues. Second, a random library of 4–15 amino acids fused to a LexA DNA binding domain was constructed and screened according to this strategy (FIG. 2D). Surprisingly, all of the third amino acid residues from the C-termini were serine, and the results of C-terminal amino acid analyses were identical to the screening of the semi-random cDNA libraries. No other significant amino acid sequences were found in these library screenings, suggesting that the motifs of the last three amino acids (tS-X-V/L/I) (SEQ ID NO: 34) are very important for the association with the third PDZ domain of FAP-1 and play a crucial role in protein-protein interaction as well as for the regulation of Fas-induced apoptosis. To further confirm whether the last three amino acids are necessary and sufficient for Fas/FAP-1 binding, plasmids of the LexA-SLV, -PLy, -PLY, -SLY, and -SLA fusion proteins were constructed and co-transformed into yeast with pVP16-FAP-1. The results showed that only LexA-SLV associated with FAP-1, whereas LexA-PLV, -PLY, -SLY, and -SLA did not (FIG. 4A). In vitro binding studies using various GST-tripeptide fusions and in vitro-translated FAP-1 were consistent with these results (FIG. 4B).

In addition to yeast two-hybrid approaches, in vitro inhibition assay of Fas/FAP-1 binding was also used. First, a synthetic peptide of the C-terminal 15 amino acids was tested whether it could inhibit the binding of Fas and FAP-1 in vitro (FIG. 3A). The binding of in vitro-translated FAP-1 to GST-Fas was dramatically reduced and dependent on the concentration of the synthetic 15 amino acids of Fas. In contrast with these results, human PAMP peptide (Kitamura, et al. 1994) as a negative control had no effect on Fas/FAP-1 binding activity under the same biochemical conditions. Second, the effect of truncated C-terminal synthetic peptides of Fas on Fas/FAP-1 binding in vitro was examined. As shown in FIG. 3B, only the three C-terminal amino acids (Ac-SLV) were sufficient to obtain the same level of inhibitory effect on the binding of FAP-1 to Fas as achieved with the 4–15 synthetic peptides. Furthermore, Fas/FAP-1 binding was extensively investigated using the scanned tripeptides to determine the critical amino acids residues required for inhibition (FIG. 3C). The results revealed that the third amino acids residues from the C-terminus, and the C-terminal amino acids having the strongest inhibitory effect were either serine or threonine; and either valine, leucine, or isoleucine, respectively. However, there were no differences among the second amino acid residues from the C-terminus with respect to their inhibitory effect on Fas/FAP-1 binding. These results were consistent with those of the yeast two-hybrid system (FIGS. 2C and 2D). Therefore, it was concluded that the C-terminal three amino acids (SLV) are critical determinants of Fas binding to the third PDZ domain of FAP-1 protein.

To further substantiate that the PDZ domain interacts with tS/T-X-V/L/I(SEQ ID NO: 4) under more native conditions, GST-fused FAP-l proteins were tested for their ability to interact with Fas expressed in Jurkat T-cells. The results revealed that the tripeptide Ac-SLV, but not Ac-SLY, abolished in a dose-dependent manner the binding activity of FAP-1 to Fas proteins extracted from Jurkat T-cells (FIGS. 4C and 4D). This suggests that the C-terminal amino acids tSLV are the minimum binding site for FAP-1, and that the amino acids serine and valine are critical for this physical association.

To next examine the hypothesis that the physiological association between the C-terminal three amino acids of Fas and the third PDZ domain of FAP-1 is necessary for the in vivo function of FAP-1 as a negative regulator of Fas-mediated signal transduction, a microinjection experiment was employed with synthetic tripeptides in a colon cancer cell line, DLD-1, which expresses both Fas and FAP-1, and is resistant to Fas-induced apoptosis. The experiments involved the direct microinjection of the synthetic tripeptides into the cytoplasmic regions of single cells and the monitoring of the physiological response to Fas-induced apoptosis in vivo. The results showed that microinjection of Ac-SLV into DLD-1 cells dramatically induced apoptosis in the presence of Fas-monoclonal antibodies (CH11, 500 ng/ml) (FIGS. 5A, 5E and FIG. 6), but that microinjection of Ac-SLY and PBS/K did not (FIGS. 5B, 5F and FIG. 6). These results strongly support the hypothesis that the physical association of FAP-1 with the C-terminus of Fas is essential for protecting cells from Fas-induced apoptosis.

In summary, it was found that the C-terminal SLV of Fas is alone necessary and sufficient for binding to the third PDZ domain of FAP-1. Secondly, it is proposed that the new consensus motif of tS/T-X-V/L/I(SEQ ID NO: 4) for such binding to the PDZ domain, instead of tS/T-X-V(SEQ ID NO: 35). It is therefore possible that FAP-l plays important roles for the modulation of signal transduction pathways in addition to its physical interaction with Fas. Thirdly, it is demonstrated that the targeted induction of Fas-mediated apoptosis in colon cancer cells by direct microinjection of the tripeptide Ac-SLV. Further investigations including the identification of a substrate(s) of FAP-1 and structure-function analysis will provide insight to the potential therapeutic applications of Fas/FAP-1 interaction in cancer as well as provide a better understanding of the inhibitory effect of FAP-1 on Fas-mediated signal transduction.

REFERENCES

1. Banville, D., et al. *J. Biol. Chem.* 269: 22320–22327 (1994).
2. Boldin, M. P. et al. *J. Biol. Chem.* 270: 7795–7798 (1995).
3. Camerini, D., et al. *J. Immunol.* 147: 3165–3169 (1991).
4. Chao, M. V. and B. L. Hempstead *TINS* 18: 321–326 (1995).
5. Chinnaiyan, A. M., et al. *Cell* 81: 505–512 (1995).
6. Cho, K. -O., et al. *Neuron* 9: 929–942 (1992).
7. Conboy, J. G., et al. *J. Biol. Chem.* 266: 8273–8280 (1991).
8. Doyle, D. A., et al. *Cell* 85: 1067–1076 (1996).
9. Funayama, N., et al. *J. Cell Biol.* 115: 1039–1048 (1991).
10. Gould, K. L., et al. *EMBO J.* 8: 4133–4142 (1989).
11. Gu, M. X., et ak. *Proc. Natl. Acad. Sci. U.S.A.* 88: 5867–5871 (1991).
12. Hill, D. E., et al. *Meth. Enzmol.* 155, 558–568 (1987).
13. Ito, N., and Magata, S. *J. Biol. Chem.* 268: 10932–10937 (1993)
14. Itoh, N. et al. *Cell* 66: 233–243 (1991).
15. Johnson, D. et al. *Cell* 47: 545–554 (1986).
16. Kim, E., et al. *Nature* 378: 85–88 (1995).
17. Kischkel, F. C. et al. *EMBO J.* 14: 5579–5588 (1995).
18. Kitamura, K. et al. *FEBS Lett*. 351: 35–37 (1994).
19. Kornau, H. -C., et al. *Science* 269:1737–1740 (1995).
20. Lankes, W. T., and Furthmayr, H. *Proc. Natl. Acad. Sci. U.S.A.* 88: 8297–8301 (1991).
21. Maekawa, K., et al. *FEBS Letters* 337: 200–206 (1994).
22. Mallett, S., et al. *EMBO J*. 9: 1063–1068 (1990).
23. Matsumine, A. et al. *Science* 272: 1020–1023 (1996).
24. McGahon, A. J. et al. *Meth. Cell Biol.* 46: 153–185 (1995).
25. Pantel, K. et al. *J. Natl. Cancer Inst.* 87: 1162–1168 (1995).
26. Rouleau, G. et al. *Nature* 363: 515–521 (1993).
27.
28. Sambrook, J., et al. (1989) *Molecular Cloning: a laboratory manual, Second Edition*, Cold Spring Harbor Laboratory Press.
29. Sato, T., et al. *Science* 268: 411–415 (1995).
30. Schnorrenberg, G. and Gerhardt H. *Tetrahedron* 45: 7759–7764 (1989).
31. Saras, J., et al. *J. Biol. Chem.* 269, 24082–24089 (1994).
32. Smith, C. A. et al. *Cell* 73: 1349–1360 (1993).
33. Stamenkovic, I., et al. *EMBO J.* 8: 1403–1410 (1989).
34. Stanger, B. Z., et al. *Cell* 81: 513–523 (1995).
35. Takahashi, T. et al. *Cell* 76: 969–976 (1994).
36. Vogel, W., et al. (1993). *Science* 259: 1611–1614 (1993).
37. Watanabe-Fukunaga, R., et al. *Nature* 356: 314–317 (1992).
38. Wang, X. W., et al. *Cancer Res.* 55: 6012–6016 (1995).
39. Westendorp, M. O. et al. *Nature* 375: 497–500 (1995).
40. Woods, D. F. and Bryant, P. J. *Cell* 66: 451–464 (1991).
41. Yang, Q., and Tonks, N. K. *Proc. Natl. Acad. Sci. U.S.A.* 88: 5949–5953 (1991).

What is claimed is:

1. A composition comprising a peptide which consists of consecutive amino acids, wherein the sequence of the consecutive amino acids is TIQSVI (SEQ ID NO: 9).

2. A composition comprising a peptide which, at the peptide's carboxyl terminus, consists of consecutive amino acids, wherein the sequence of the consecutive amino acids is selected from the group consisting of RETIESTV (SEQ ID NO: 11), QNFRTYIVSFV (SEQ ID NO: 12), PPTCSQANSGRISTL (SEQ ID NO: 14), IDLASEFLFLSNSFL (SEQ ID NO: 15) and DSEMYNFRSQLASVV (SEQ ID NO: 16), wherein the peptide inhibits binding between Fas and Fas-associated phosphatase-1 (Fap-1).

3. A composition comprising a peptide which consists of consecutive amino acids, wherein the sequence of the consecutive amino acids is SDSNMNMNELSEV (SEQ ID NO: 13).

* * * * *

SEQUENCE LISTING

```
<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
<223> OTHER INFORMATION: Xaa=Gly, Ser, Ala or Glu
<220> FEATURE:
<221> NAME/KEY: SITE
<222> LOCATION: (4)
<223> OTHER INFORMATION: Xaa=Phe, Ile or Leu

<400> SEQUENCE: 1

Xaa Leu Gly Xaa
 1

<210> SEQ ID NO 2
<211> LENGTH: 9
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
```

```
<223> OTHER INFORMATION: Xaa=Lys, Arg or Gln
<220> FEATURE:
<221> NAME/KEY: SITE
<222> LOCATION: (2)..(5)
<223> OTHER INFORMATION: Xaa=any amino acid, up to 2 Xaa may be missing
<220> FEATURE:
<221> NAME/KEY: SITE
<222> LOCATION: (6)
<223> OTHER INFORMATION: Xaa=Gly, Ser, Ala or Glu
<220> FEATURE:
<221> NAME/KEY: SITE
<222> LOCATION: (9)
<223> OTHER INFORMATION: Xaa=Phe, Ile or Leu

<400> SEQUENCE: 2

Xaa Xaa Xaa Xaa Xaa Xaa Leu Gly Xaa
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial
      Sequence:source:synthesized

<400> SEQUENCE: 3

Ser Leu Gly Ile
 1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
<223> OTHER INFORMATION: Xaa=Ser or Thr
<220> FEATURE:
<221> NAME/KEY: SITE
<222> LOCATION: (2)
<223> OTHER INFORMATION: Xaa=any one amino acid
<220> FEATURE:
<221> NAME/KEY: SITE
<222> LOCATION: (3)
<223> OTHER INFORMATION: Xaa=Val, Ile or Leu

<400> SEQUENCE: 4

Xaa Xaa Xaa
 1

<210> SEQ ID NO 5
<211> LENGTH: 15
<212> TYPE: PRT
<213> ORGANISM: human

<400> SEQUENCE: 5

Asp Ser Glu Asn Ser Asn Phe Arg Asn Glu Ile Gln Ser Leu Val
 1               5                  10                  15

<210> SEQ ID NO 6
<211> LENGTH: 15
<212> TYPE: PRT
<213> ORGANISM: rat

<400> SEQUENCE: 6

Ser Ile Ser Asn Ser Arg Asn Glu Asn Glu Gly Gln Ser Leu Glu
```

-continued

```
<210> SEQ ID NO 7
<211> LENGTH: 15
<212> TYPE: PRT
<213> ORGANISM: mouse

<400> SEQUENCE: 7

Ser Thr Pro Asp Thr Gly Asn Glu Asn Glu Gly Gln Cys Leu Glu
  1               5                  10                  15

<210> SEQ ID NO 8
<211> LENGTH: 4
<212> TYPE: PRT
<213> ORGANISM: Artificial Sequence
<220> FEATURE:
<223> OTHER INFORMATION: Description of Artificial
      Sequence:source:synthesized

<400> SEQUENCE: 8

Glu Ser Leu Val
  1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:
      source:synthesized

<400> SEQUENCE: 9

Thr Ile Gln Ser Val Ile
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 10

Arg Gly Phe Ile Ser Ser Leu Val
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 11

Arg Glu Thr Ile Glu Ser Thr Val
  1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial
      Sequence:source:synthesized

<400> SEQUENCE: 12
```

```
Gln Asn Phe Arg Thr Tyr Ile Val Ser Phe Val
 1               5                  10
```

<210> SEQ ID NO 13
<211> LENGTH: 13
<212> TYPE: PRT
<213> ORGANISM: Artificial Sequence
<220> FEATURE:
<223> OTHER INFORMATION: Description of Artificial
      Sequence:source:synthesized

<400> SEQUENCE: 13

```
Ser Asp Ser Asn Met Asn Met Asn Glu Leu Ser Glu Val
 1               5                  10
```

<210> SEQ ID NO 14
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 14

```
Pro Pro Thr Cys Ser Gln Ala Asn Ser Gly Arg Ile Ser Thr Leu
 1               5                  10                  15
```

<210> SEQ ID NO 15
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 15

```
Ile Asp Leu Ala Ser Glu Phe Leu Phe Leu Ser Asn Ser Phe Leu
 1               5                  10                  15
```

<210> SEQ ID NO 16
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 16

```
Asp Ser Glu Met Tyr Asn Phe Arg Ser Gln Leu Ala Ser Val Val
 1               5                  10                  15
```

<210> SEQ ID NO 17
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 17

```
Ile Pro Pro Asp Ser Glu Asp Gly Asn Glu Glu Gln Ser Leu Val
 1               5                  10                  15
```

<210> SEQ ID NO 18
<211> LENGTH: 4
<212> TYPE: PRT
<213> ORGANISM: Artificial Sequence

```
<220> FEATURE:
<223> OTHER INFORMATION: Description of Artificial
      Sequence:source:synthesized

<400> SEQUENCE: 18

Gln Ser Leu Val
 1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:source
      synthesized

<400> SEQUENCE: 19

Ile Gln Ser Leu Val
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial
      Sequence:source:synthesized

<400> SEQUENCE: 20

Glu Ile Gln Ser Leu Val
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial
      Sequence:source:synthesized

<400> SEQUENCE: 21

Asn Glu Ile Gln Ser Leu Val
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 22

Arg Asn Glu Ile Gln Ser Leu Val
 1               5

<210> SEQ ID NO 23
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 23

Asp Ser Glu Asn Ser Asn Phe Arg Asn Glu Ile Gln Ser Leu Val
 1               5                  10                  15
```

```
<210> SEQ ID NO 24
<211> LENGTH: 427
<212> TYPE: PRT
<213> ORGANISM: human

<400> SEQUENCE: 24
```

| | | | | | | | | | | | | | | |
|---|---|---|---|---|---|---|---|---|---|---|---|---|---|---|
|Met|Gly|Ala|Gly|Ala|Thr|Gly|Arg|Ala|Met|Asp|Gly|Pro|Arg|Leu|Leu|
|1| | | |5| | | | |10| | | | |15| |

Leu Leu Leu Leu Leu Gly Val Ser Leu Gly Gly Ala Lys Glu Ala Cys
              20                    25                    30

Pro Thr Gly Leu Tyr Thr His Ser Gly Glu Cys Cys Lys Ala Cys Asn
        35                    40                    45

Leu Gly Glu Gly Val Ala Gln Pro Cys Gly Ala Asn Gln Thr Val Cys
   50                    55                    60

Glu Pro Cys Leu Asp Ser Val Thr Phe Ser Asp Val Val Ser Ala Thr
65                70                75              80

Glu Pro Cys Lys Pro Cys Thr Glu Cys Val Gly Leu Gln Ser Met Ser
            85                90              95

Ala Pro Cys Val Glu Ala Asp Asp Ala Val Cys Arg Cys Ala Tyr Gly
        100                105              110

Tyr Tyr Gln Asp Glu Thr Thr Gly Arg Cys Glu Ala Cys Arg Val Cys
      115                120              125

Glu Ala Gly Ser Gly Leu Val Phe Ser Cys Gln Asp Lys Gln Asn Thr
   130                 135              140

Val Cys Glu Glu Cys Pro Asp Gly Thr Tyr Ser Asp Glu Ala Asn His
145                150              155              160

Val Asp Pro Cys Leu Pro Cys Thr Val Cys Glu Asp Thr Glu Arg Gln
        165                170              175

Leu Arg Glu Cys Thr Arg Trp Ala Asp Ala Glu Cys Glu Glu Ile Pro
      180                185              190

Gly Arg Trp Ile Thr Arg Ser Thr Pro Pro Glu Gly Ser Asp Ser Thr
   195                 200              205

Ala Pro Ser Thr Gln Glu Pro Glu Ala Pro Pro Glu Gln Asp Leu Ile
210                215              220

Ala Ser Thr Val Ala Gly Val Val Thr Thr Val Met Gly Ser Ser Gln
225                230              235              240

Pro Val Val Thr Arg Gly Thr Thr Asp Asn Leu Ile Pro Val Tyr Cys
        245                250              255

Ser Ile Leu Ala Ala Val Val Val Gly Leu Val Ala Tyr Ile Ala Phe
      260                265              270

Lys Arg Trp Asn Ser Cys Lys Gln Asn Lys Gly Gly Ala Asn Ser Arg
   275                 280              285

Pro Val Asn Gln Thr Pro Pro Pro Glu Gly Glu Lys Ile His Ser Asp
290                295              300

Ser Gly Ile Ser Val Asp Ser Gln Ser Leu His Asp Gln Gln Pro His
305                310              315              320

Thr Gln Thr Ala Ser Gly Gln Ala Leu Lys Gly Asp Gly Gly Leu Tyr
        325                330              335

Ser Ser Leu Pro Pro Ala Lys Arg Glu Glu Val Glu Lys Leu Leu Asn
        340                345              350

Gly Ser Ala Gly Asp Thr Trp Arg His Leu Ala Gly Glu Leu Gly Tyr
   355                 360              365

Gln Pro Glu His Ile Asp Ser Phe Thr His Glu Ala Cys Pro Val Arg
   370                 375              380

```
Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425
```

<210> SEQ ID NO 25
<211> LENGTH: 458
<212> TYPE: PRT
<213> ORGANISM: human

<400> SEQUENCE: 25

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Ile Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
        210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
        290                 295                 300

Thr Gly Lys Leu His Gln Glu Asn Val Leu Val Val Met Arg Ala Thr
305                 310                 315                 320

Gln Leu Gln Lys Asn Leu Thr Cys Glu Val Trp Gly Pro Thr Ser Pro
```

```
                    325                 330                 335
Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
                355                 360                 365

Gln Cys Leu Leu Ser Asp Ser Gly Gln Val Leu Leu Glu Ser Asn Ile
                370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                    405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Glu Cys Gln Cys Pro
                435                 440                 445

His Arg Phe Gln Lys Thr Cys Ser Pro Ile
                450                 455

<210> SEQ ID NO 26
<211> LENGTH: 828
<212> TYPE: PRT
<213> ORGANISM: human

<400> SEQUENCE: 26

Met Asn Ser Gly Val Ala Met Lys Tyr Gly Asn Asp Ser Ser Ala Glu
1               5                   10                  15

Leu Ser Glu Leu His Ser Ala Leu Ala Ser Leu Lys Gly Asp Ile
                20                  25                  30

Val Glu Leu Asn Lys Arg Leu Gln Gln Thr Glu Arg Glu Asp Leu Leu
            35                  40                  45

Glu Lys Lys Leu Ala Lys Ala Gln Cys Glu Gln Ser His Leu Met Arg
        50                  55                  60

Glu His Glu Asp Val Gln Glu Arg Thr Thr Leu Arg Tyr Glu Glu Arg
65                  70                  75                  80

Ile Thr Glu Leu His Ser Val Ile Ala Glu Leu Asn Lys Lys Ile Asp
                85                  90                  95

Arg Leu Gln Gly Thr Thr Ile Arg Glu Glu Asp Glu Tyr Ser Glu Leu
                100                 105                 110

Arg Ser Glu Leu Ser Gln Ser Gln His Glu Val Asn Glu Asp Ser Arg
            115                 120                 125

Ser Met Asp Gln Asp Gln Thr Ser Val Ser Ile Pro Glu Asn Gln Ser
        130                 135                 140

Thr Met Val Thr Ala Asp Met Asp Asn Cys Ser Asp Ile Asn Ser Glu
145                 150                 155                 160

Leu Gln Arg Val Leu Thr Gly Leu Glu Asn Val Val Cys Gly Arg Lys
                165                 170                 175

Lys Ser Ser Cys Ser Leu Ser Val Ala Glu Val Asp Arg His Ile Glu
                180                 185                 190

Gln Leu Thr Thr Ala Ser Glu His Cys Asp Leu Ala Ile Lys Thr Val
            195                 200                 205

Glu Glu Ile Glu Gly Val Leu Gly Arg Asp Leu Tyr Pro Asn Leu Ala
        210                 215                 220

Glu Glu Arg Ser Arg Trp Glu Lys Glu Leu Ala Gly Leu Arg Glu Glu
225                 230                 235                 240
```

-continued

```
Asn Glu Ser Leu Thr Ala Met Leu Cys Ser Lys Glu Glu Leu Asn
            245                 250                 255
Arg Thr Lys Ala Thr Met Asn Ala Ile Arg Glu Arg Asp Arg Leu
            260                 265                 270
Arg Arg Arg Val Arg Glu Leu Gln Thr Arg Leu Gln Ser Val Gln Ala
        275                 280                 285
Thr Gly Pro Ser Ser Pro Gly Arg Leu Thr Ser Thr Asn Arg Pro Ile
        290                 295                 300
Asn Pro Ser Thr Gly Glu Leu Ser Thr Ser Ser Ser Asn Asp Ile
305                 310                 315                 320
Pro Ile Ala Lys Ile Ala Glu Arg Val Lys Leu Ser Lys Thr Arg Ser
            325                 330                 335
Glu Ser Ser Ser Ser Asp Arg Pro Val Leu Gly Ser Glu Ile Ser Ser
            340                 345                 350
Ile Gly Val Ser Ser Ser Val Ala Glu His Leu Ala His Ser Leu Gln
        355                 360                 365
Asp Cys Ser Asn Ile Gln Glu Ile Phe Gln Thr Leu Tyr Ser His Gly
        370                 375                 380
Ser Ala Ile Ser Glu Ser Lys Ile Arg Glu Phe Glu Val Glu Thr Glu
385                 390                 395                 400
Arg Leu Asn Ser Arg Ile Glu His Leu Lys Ser Gln Asn Asp Leu Leu
            405                 410                 415
Thr Ile Thr Leu Glu Glu Cys Lys Ser Asn Ala Glu Arg Met Ser Met
            420                 425                 430
Leu Val Gly Lys Tyr Glu Ser Asn Ala Thr Ala Leu Arg Leu Ala Leu
        435                 440                 445
Gln Tyr Ser Glu Gln Cys Ile Glu Ala Tyr Glu Leu Leu Leu Ala Leu
        450                 455                 460
Ala Glu Ser Glu Gln Ser Leu Ile Leu Gly Gln Phe Arg Ala Ala Gly
465                 470                 475                 480
Val Gly Ser Ser Pro Gly Asp Gln Ser Gly Asp Glu Asn Ile Thr Gln
            485                 490                 495
Met Leu Lys Arg Ala His Asp Cys Arg Lys Thr Ala Glu Asn Ala Ala
            500                 505                 510
Lys Ala Leu Leu Met Lys Leu Asp Gly Ser Cys Gly Gly Ala Phe Ala
        515                 520                 525
Val Ala Gly Cys Ser Val Gln Pro Trp Glu Ser Leu Ser Ser Asn Ser
        530                 535                 540
His Thr Ser Thr Thr Ser Ser Thr Ala Ser Ser Cys Asp Thr Glu Phe
545                 550                 555                 560
Thr Lys Glu Asp Glu Gln Arg Leu Lys Asp Tyr Ile Gln Gln Leu Lys
            565                 570                 575
Asn Asp Arg Ala Ala Val Lys Leu Thr Met Leu Glu Leu Glu Ser Ile
            580                 585                 590
His Ile Asp Pro Leu Ser Tyr Asp Val Lys Pro Arg Gly Asp Ser Gln
        595                 600                 605
Arg Leu Asp Leu Glu Asn Ala Val Leu Met Gln Leu Met Ala Met
        610                 615                 620
Lys Glu Glu Met Ala Glu Leu Lys Ala Gln Leu Tyr Leu Leu Glu Lys
625                 630                 635                 640
Glu Lys Lys Ala Leu Glu Leu Lys Leu Ser Thr Arg Glu Ala Gln Glu
            645                 650                 655
Gln Ala Tyr Leu Val His Ile Glu His Leu Lys Ser Glu Val Glu Glu
```

```
                660                 665                 670
Gln Lys Glu Gln Arg Met Arg Ser Leu Ser Thr Ser Ser Gly Ser
            675                 680                 685

Lys Asp Lys Pro Gly Lys Glu Cys Ala Asp Ala Ala Ser Pro Ala Leu
            690                 695                 700

Ser Leu Ala Glu Leu Arg Thr Thr Cys Ser Glu Asn Glu Leu Ala Ala
705                 710                 715                 720

Glu Phe Thr Asn Ala Ile Arg Arg Glu Lys Leu Lys Ala Arg Val
                725                 730                 735

Gln Glu Leu Val Ser Ala Leu Glu Arg Leu Thr Lys Ser Ser Glu Ile
            740                 745                 750

Arg His Gln Gln Ser Ala Glu Phe Val Asn Asp Leu Lys Arg Ala Asn
                755                 760                 765

Ser Asn Leu Val Ala Ala Tyr Glu Lys Ala Lys Lys His Gln Asn
            770                 775                 780

Lys Leu Lys Lys Leu Glu Ser Gln Met Met Ala Met Val Glu Arg His
785                 790                 795                 800

Glu Thr Gln Val Arg Met Leu Lys Gln Arg Ile Ala Leu Leu Glu Glu
                805                 810                 815

Glu Asn Ser Arg Pro His Thr Asn Glu Thr Ser Leu
            820                 825

<210> SEQ ID NO 27
<211> LENGTH: 672
<212> TYPE: PRT
<213> ORGANISM: human

<400> SEQUENCE: 27

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gly Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205
```

```
Lys Gln Lys Thr Lys Thr Ile Arg Ser Thr Leu Asn Pro Gln Trp Asn
210                 215                 220
Glu Ser Phe Thr Phe Lys Leu Lys Pro Ser Asp Lys Asp Arg Arg Leu
225                 230                 235                 240
Ser Val Glu Ile Trp Asp Trp Asp Arg Thr Thr Arg Asn Asp Phe Met
                245                 250                 255
Gly Ser Leu Ser Phe Gly Val Ser Glu Leu Met Lys Met Pro Ala Ser
                260                 265                 270
Gly Trp Tyr Lys Leu Leu Asn Gln Glu Glu Gly Glu Tyr Tyr Asn Val
            275                 280                 285
Pro Ile Pro Glu Gly Asp Glu Gly Asn Met Glu Leu Arg Gln Lys
290                 295                 300
Phe Glu Lys Ala Lys Leu Gly Pro Ala Gly Asn Lys Val Ile Ser Pro
305                 310                 315                 320
Ser Glu Asp Arg Lys Gln Pro Ser Asn Asn Leu Asp Arg Val Lys Leu
                325                 330                 335
Thr Asp Phe Asn Phe Leu Met Val Leu Gly Lys Gly Ser Phe Gly Lys
                340                 345                 350
Val Met Leu Ala Asp Arg Lys Gly Thr Glu Glu Leu Tyr Ala Ile Lys
            355                 360                 365
Ile Leu Lys Lys Asp Val Val Ile Gln Asp Asp Asp Val Glu Cys Thr
370                 375                 380
Met Val Glu Lys Arg Val Leu Ala Leu Leu Asp Lys Pro Pro Phe Leu
385                 390                 395                 400
Thr Gln Leu His Ser Cys Phe Gln Thr Val Asp Arg Leu Tyr Phe Val
                405                 410                 415
Met Glu Tyr Val Asn Gly Gly Asp Leu Met Tyr His Ile Gln Gln Val
                420                 425                 430
Gly Lys Phe Lys Glu Pro Gln Ala Val Phe Tyr Ala Ala Glu Ile Ser
            435                 440                 445
Ile Gly Leu Phe Phe Leu His Lys Arg Gly Ile Ile Tyr Arg Asp Leu
450                 455                 460
Lys Leu Asp Asn Val Met Leu Asp Ser Glu Gly His Ile Lys Ile Ala
465                 470                 475                 480
Asp Phe Gly Met Cys Lys Glu His Met Met Asp Gly Val Thr Thr Arg
                485                 490                 495
Thr Phe Cys Gly Thr Pro Asp Tyr Ile Ala Pro Glu Ile Ile Ala Tyr
                500                 505                 510
Gln Pro Tyr Gly Lys Ser Val Asp Trp Trp Ala Tyr Gly Val Leu Leu
            515                 520                 525
Tyr Glu Met Leu Ala Gly Gln Pro Pro Phe Asp Gly Glu Asp Glu Asp
            530                 535                 540
Glu Leu Phe Gln Ser Ile Met Glu His Asn Val Ser Tyr Pro Lys Ser
545                 550                 555                 560
Leu Ser Lys Glu Ala Val Ser Ile Cys Lys Gly Leu Met Thr Lys His
                565                 570                 575
Pro Ala Lys Arg Leu Gly Cys Gly Pro Glu Gly Glu Arg Asp Val Arg
                580                 585                 590
Glu His Ala Phe Phe Arg Arg Ile Asp Trp Glu Lys Leu Glu Asn Arg
            595                 600                 605
Glu Ile Gln Pro Pro Phe Lys Pro Lys Val Cys Gly Lys Gly Ala Glu
            610                 615                 620
Asn Phe Asp Lys Phe Phe Thr Arg Gly Gln Pro Val Leu Thr Pro Pro
```

```
                625                 630                 635                 640
Asp Gln Leu Val Ile Ala Asn Ile Asp Gln Ser Asp Phe Glu Gly Phe
                        645                 650                 655
Ser Tyr Val Asn Pro Gln Phe Val His Pro Ile Leu Gln Ser Ala Val
                660                 665                 670

<210> SEQ ID NO 28
<211> LENGTH: 471
<212> TYPE: PRT
<213> ORGANISM: human

<400> SEQUENCE: 28

Met Asp Ile Leu Cys Glu Glu Asn Thr Ser Leu Ser Ser Thr Thr Asn
 1               5                  10                  15
Ser Leu Met Gln Leu Asn Asp Asp Thr Arg Leu Tyr Ser Asn Asp Phe
                20                  25                  30
Asn Ser Gly Glu Ala Asn Thr Ser Asp Ala Phe Asn Trp Thr Val Asp
            35                  40                  45
Ser Glu Asn Arg Thr Asn Leu Ser Cys Glu Gly Cys Leu Ser Pro Ser
        50                  55                  60
Cys Leu Ser Leu Leu His Leu Gln Glu Lys Asn Trp Ser Ala Leu Leu
65                  70                  75                  80
Thr Ala Val Val Ile Ile Leu Thr Ile Ala Gly Asn Ile Leu Val Ile
                85                  90                  95
Met Ala Val Ser Leu Glu Lys Lys Leu Gln Asn Ala Thr Asn Tyr Phe
            100                 105                 110
Leu Met Ser Leu Ala Ile Ala Asp Met Leu Leu Gly Phe Leu Val Met
        115                 120                 125
Pro Val Ser Met Leu Thr Ile Leu Tyr Gly Tyr Arg Trp Pro Leu Pro
    130                 135                 140
Ser Lys Leu Cys Ala Val Trp Ile Tyr Leu Asp Val Leu Phe Ser Thr
145                 150                 155                 160
Ala Ser Ile Met His Leu Cys Ala Ile Ser Leu Asp Arg Tyr Val Ala
                165                 170                 175
Ile Gln Asn Pro Ile His His Ser Arg Phe Asn Ser Arg Thr Lys Ala
            180                 185                 190
Phe Leu Lys Ile Ile Ala Val Trp Thr Ile Ser Val Gly Ile Ser Met
        195                 200                 205
Pro Ile Pro Val Phe Gly Leu Gln Asp Asp Ser Lys Val Phe Lys Glu
    210                 215                 220
Gly Ser Cys Leu Leu Ala Asp Asp Asn Phe Val Leu Ile Gly Ser Phe
225                 230                 235                 240
Val Ser Phe Phe Ile Pro Leu Thr Ile Met Val Ile Thr Tyr Phe Leu
                245                 250                 255
Thr Ile Lys Ser Leu Gln Lys Glu Ala Thr Leu Cys Val Ser Asp Leu
            260                 265                 270
Gly Thr Arg Ala Lys Leu Ala Ser Phe Ser Phe Leu Pro Gln Ser Ser
        275                 280                 285
Leu Ser Ser Glu Lys Leu Phe Gln Arg Ser Ile His Arg Glu Pro Gly
    290                 295                 300
Ser Tyr Thr Gly Arg Arg Thr Met Gln Ser Ile Ser Asn Glu Gln Lys
305                 310                 315                 320
Ala Cys Lys Val Leu Gly Ile Val Phe Phe Leu Phe Val Val Met Trp
                325                 330                 335
```

```
Cys Pro Phe Phe Ile Thr Asn Ile Met Ala Val Ile Cys Lys Glu Ser
                340                 345                 350

Cys Asn Glu Asp Val Ile Gly Ala Leu Leu Asn Val Phe Val Trp Ile
            355                 360                 365

Gly Tyr Leu Ser Ser Ala Val Asn Pro Leu Val Tyr Thr Leu Phe Asn
        370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Lys Lys Asn Ser
            420                 425                 430

Lys Gln Asp Ala Lys Thr Thr Asp Asn Asp Cys Ser Met Val Ala Leu
            435                 440                 445

Gly Lys Gln His Ser Glu Glu Ala Ser Lys Asp Asn Ser Asp Gly Val
        450                 455                 460

Asn Glu Lys Val Ser Cys Val
465                 470

<210> SEQ ID NO 29
<211> LENGTH: 481
<212> TYPE: PRT
<213> ORGANISM: human

<400> SEQUENCE: 29

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
                20                  25                  30

Gly Leu Gln Thr Glu Ser Ile Pro Glu Glu Met Lys Gln Ile Val Glu
            35                  40                  45

Glu Gln Gly Asn Lys Leu His Trp Ala Ala Leu Leu Ile Leu Met Val
        50                  55                  60

Ile Ile Pro Thr Ile Gly Gly Asn Thr Leu Val Ile Leu Ala Val Ser
65                  70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
                100                 105                 110

Leu Thr Ile Met Phe Glu Ala Met Trp Pro Leu Pro Leu Val Leu Cys
            115                 120                 125

Pro Ala Trp Leu Phe Leu Asp Val Leu Phe Ser Thr Ala Ser Ile Met
130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
210                 215                 220

Ala Phe Phe Thr Pro Leu Ala Ile Met Ile Val Thr Tyr Phe Leu Thr
225                 230                 235                 240
```

-continued

```
Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
            260                 265                 270

Thr Pro Cys Ser Ser Pro Glu Lys Val Ala Met Leu Asp Gly Ser Arg
        275                 280                 285

Lys Asp Lys Ala Leu Pro Asn Ser Gly Asp Glu Thr Leu Met Arg Arg
    290                 295                 300

Thr Ser Thr Ile Gly Lys Lys Ser Val Gln Thr Ile Ser Asn Glu Gln
305                 310                 315                 320

Arg Ala Ser Lys Val Leu Gly Ile Val Phe Phe Leu Phe Leu Leu Met
                325                 330                 335

Trp Cys Pro Phe Phe Ile Thr Asn Ile Thr Leu Val Leu Cys Asp Ser
            340                 345                 350

Cys Asn Gln Thr Thr Leu Gln Met Leu Leu Glu Ile Phe Val Trp Ile
        355                 360                 365

Gly Tyr Val Ser Ser Gly Val Asn Pro Leu Val Tyr Thr Leu Phe Asn
    370                 375                 380

Lys Thr Phe Arg Asp Ala Phe Gly Arg Tyr Ile Thr Cys Asn Tyr Arg
385                 390                 395                 400

Ala Thr Lys Ser Val Lys Thr Leu Arg Lys Arg Ser Ser Lys Ile Tyr
                405                 410                 415

Phe Arg Asn Pro Met Ala Glu Asn Ser Lys Phe Phe Lys Lys His Gly
            420                 425                 430

Ile Arg Asn Gly Ile Asn Pro Ala Met Tyr Gln Ser Pro Met Arg Leu
        435                 440                 445

Arg Ser Ser Thr Ile Gln Ser Ser Ile Ile Leu Leu Asp Thr Leu
    450                 455                 460

Leu Leu Thr Glu Asn Glu Gly Asp Lys Thr Glu Glu Gln Val Ser Tyr
465                 470                 475                 480

Val

<210> SEQ ID NO 30
<211> LENGTH: 2843
<212> TYPE: PRT
<213> ORGANISM: human

<400> SEQUENCE: 30

Met Ala Ala Ala Ser Tyr Asp Gln Leu Leu Lys Gln Val Glu Ala Leu
  1               5                  10                  15

Lys Met Glu Asn Ser Asn Leu Arg Gln Glu Leu Glu Asp Asn Ser Asn
                 20                  25                  30

His Leu Thr Lys Leu Glu Thr Glu Ala Ser Asn Met Lys Glu Val Leu
             35                  40                  45

Lys Gln Leu Gln Gly Ser Ile Glu Asp Glu Ala Met Ala Ser Ser Gly
         50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                 85                  90                  95

Gly Ser Arg Glu Gly Ser Val Ser Ser Arg Ser Gly Glu Cys Ser Pro
                100                 105                 110

Val Pro Met Gly Ser Phe Pro Arg Arg Gly Phe Val Asn Gly Ser Arg
            115                 120                 125
```

```
Glu Ser Thr Gly Tyr Leu Glu Glu Leu Glu Lys Glu Arg Ser Leu Leu
    130                 135                 140

Leu Ala Asp Leu Asp Lys Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
                180                 185                 190

Ala Arg Gln Ile Arg Val Ala Met Glu Glu Gln Leu Gly Thr Cys Gln
                195                 200                 205

Asp Met Glu Lys Arg Ala Gln Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
                260                 265                 270

Thr Ser Gly Asn Gly Gln Gly Ser Thr Thr Arg Met Asp His Glu Thr
    275                 280                 285

Ala Ser Val Leu Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
                355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Ser Thr Cys Trp Glu Trp Gln Glu Ala His Glu Pro Gly Met Asp
                420                 425                 430

Gln Asp Lys Asn Pro Met Pro Ala Pro Val Glu His Gln Ile Cys Pro
    435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
    515                 520                 525

Leu Val Ala Gln Leu Lys Ser Glu Ser Glu Asp Leu Gln Gln Val Ile
530                 535                 540
```

-continued

```
Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
            565                 570                 575

Leu Glu Val Lys Lys Glu Ser Thr Leu Lys Ser Val Leu Ser Ala Leu
        580                 585                 590

Trp Asn Leu Ser Ala His Cys Thr Glu Asn Lys Ala Asp Ile Cys Ala
    595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Ile Leu Arg
625                 630                 635                 640

Asn Val Ser Ser Leu Ile Ala Thr Asn Glu Asp His Arg Gln Ile Leu
            645                 650                 655

Arg Glu Asn Asn Cys Leu Gln Thr Leu Leu Gln His Leu Lys Ser His
        660                 665                 670

Ser Leu Thr Ile Val Ser Asn Ala Cys Gly Thr Leu Trp Asn Leu Ser
    675                 680                 685

Ala Arg Asn Pro Lys Asp Gln Glu Ala Leu Trp Asp Met Gly Ala Val
690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
            725                 730                 735

Tyr Lys Asp Ala Asn Ile Met Ser Pro Gly Ser Ser Leu Pro Ser Leu
        740                 745                 750

His Val Arg Lys Gln Lys Ala Leu Glu Ala Glu Leu Asp Ala Gln His
    755                 760                 765

Leu Ser Glu Thr Phe Asp Asn Ile Asp Asn Ile Ser Pro Lys Ala Ser
770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
            805                 810                 815

Gly Asn Met Thr Val Leu Ser Pro Tyr Leu Asn Thr Thr Val Leu Pro
        820                 825                 830

Ser Ser Ser Ser Ser Arg Gly Ser Leu Asp Ser Ser Arg Ser Glu Lys
    835                 840                 845

Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
            885                 890                 895

Ile His Thr Ser Gln Glu Asp Arg Ser Ser Gly Ser Thr Thr Glu Leu
        900                 905                 910

His Cys Val Thr Asp Glu Arg Asn Ala Leu Arg Arg Ser Ser Ala Ala
    915                 920                 925

His Thr His Ser Asn Thr Tyr Asn Phe Thr Lys Ser Glu Asn Ser Asn
930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
```

-continued

```
                965                 970                 975
Gly Gln Met Lys Pro Ser Ile Glu Ser Tyr Ser Glu Asp Asp Glu Ser
            980                 985                 990
Lys Phe Cys Ser Tyr Gly Gln Tyr Pro Ala Asp Leu Ala His Lys Ile
            995                1000                1005
His Ser Ala Asn His Met Asp Asp Asn Asp Gly Glu Leu Asp Thr Pro
           1010                1015                1020
Ile Asn Tyr Ser Leu Lys Tyr Ser Asp Glu Gln Leu Asn Ser Gly Arg
       1025                1030                1035                1040
Gln Ser Pro Ser Gln Asn Glu Arg Trp Ala Arg Pro Lys His Ile Ile
           1045                1050                1055
Glu Asp Glu Ile Lys Gln Ser Glu Gln Arg Gln Ser Arg Asn Gln Ser
           1060                1065                1070
Thr Thr Tyr Pro Val Tyr Thr Glu Ser Thr Asp Asp Lys His Leu Lys
           1075                1080                1085
Phe Gln Pro His Phe Gly Gln Gln Glu Cys Val Ser Pro Tyr Arg Ser
           1090                1095                1100
Arg Gly Ala Asn Gly Ser Glu Thr Asn Arg Val Gly Ser Asn His Gly
       1105                1110                1115                1120
Ile Asn Gln Asn Val Ser Gln Ser Leu Cys Gln Glu Asp Asp Tyr Glu
           1125                1130                1135
Asp Asp Lys Pro Thr Asn Tyr Ser Glu Arg Tyr Ser Glu Glu Gln Gln
           1140                1145                1150
His Glu Glu Glu Arg Pro Thr Asn Tyr Ser Ile Lys Tyr Asn Glu
           1155                1160                1165
Glu Lys Arg His Val Asp Gln Pro Ile Asp Tyr Ser Ile Leu Lys Ala
           1170                1175                1180
Thr Asp Ile Pro Ser Ser Gln Lys Gln Ser Phe Ser Phe Ser Lys Ser
       1185                1190                1195                1200
Ser Ser Gly Gln Ser Ser Lys Thr Glu His Met Ser Ser Ser Ser Glu
           1205                1210                1215
Asn Thr Ser Thr Pro Ser Ser Asn Ala Lys Arg Gln Asn Gln Leu His
           1220                1225                1230
Pro Ser Ser Ala Gln Ser Arg Ser Gly Gln Pro Gln Lys Ala Ala Thr
           1235                1240                1245
Cys Lys Val Ser Ser Ile Asn Gln Glu Thr Ile Gln Thr Tyr Cys Val
       1250                1255                1260
Glu Asp Thr Pro Ile Cys Phe Ser Arg Cys Ser Ser Leu Ser Ser Leu
       1265                1270                1275                1280
Ser Ser Ala Glu Asp Glu Ile Gly Cys Asn Gln Thr Thr Gln Glu Ala
           1285                1290                1295
Asp Ser Ala Asn Thr Leu Gln Ile Ala Glu Ile Lys Glu Lys Ile Gly
           1300                1305                1310
Thr Arg Ser Ala Glu Asp Pro Val Ser Glu Val Pro Ala Val Ser Gln
           1315                1320                1325
His Pro Arg Thr Lys Ser Ser Arg Leu Gln Gly Ser Ser Leu Ser Ser
           1330                1335                1340
Glu Ser Ala Arg His Lys Ala Val Glu Phe Ser Ser Gly Ala Lys Ser
       1345                1350                1355                1360
Pro Ser Lys Ser Gly Ala Gln Thr Pro Lys Ser Pro Glu His Tyr
           1365                1370                1375
Val Gln Glu Thr Pro Leu Met Phe Ser Arg Cys Thr Ser Val Ser Ser
           1380                1385                1390
```

-continued

```
Leu Asp Ser Phe Glu Ser Arg Ser Ile Ala Ser Ser Val Gln Ser Glu
        1395                1400                1405
Pro Cys Ser Gly Met Val Ser Gly Ile Ile Ser Pro Ser Asp Leu Pro
    1410                1415                1420
Asp Ser Pro Gly Gln Thr Met Pro Pro Ser Arg Ser Lys Thr Pro Pro
1425                1430                1435                1440
Pro Pro Pro Gln Thr Ala Gln Thr Lys Arg Glu Val Pro Lys Asn Lys
            1445                1450                1455
Ala Pro Thr Ala Glu Lys Arg Glu Ser Gly Pro Lys Gln Ala Ala Val
        1460                1465                1470
Asn Ala Ala Val Gln Arg Val Gln Val Leu Pro Asp Ala Asp Thr Leu
    1475                1480                1485
Leu His Phe Ala Thr Glu Ser Thr Pro Asp Gly Phe Ser Cys Ser Ser
1490                1495                1500
Ser Leu Ser Ala Leu Ser Leu Asp Glu Pro Phe Ile Gln Lys Asp Val
1505                1510                1515                1520
Glu Leu Arg Ile Met Pro Pro Val Gln Glu Asn Asp Asn Gly Asn Glu
            1525                1530                1535
Thr Glu Ser Glu Gln Pro Lys Glu Ser Asn Glu Asn Gln Glu Lys Glu
        1540                1545                1550
Ala Glu Lys Thr Ile Asp Ser Glu Lys Asp Leu Leu Asp Asp Ser Asp
    1555                1560                1565
Asp Asp Asp Ile Glu Ile Leu Glu Glu Cys Ile Ile Ser Ala Met Pro
1570                1575                1580
Thr Lys Ser Ser Arg Lys Ala Lys Lys Pro Ala Gln Thr Ala Ser Lys
1585                1590                1595                1600
Leu Pro Pro Pro Val Ala Arg Lys Pro Ser Gln Leu Pro Val Tyr Lys
            1605                1610                1615
Leu Leu Pro Ser Gln Asn Arg Leu Gln Pro Gln Lys His Val Ser Phe
        1620                1625                1630
Thr Pro Gly Asp Asp Met Pro Arg Val Tyr Cys Val Glu Gly Thr Pro
    1635                1640                1645
Ile Asn Phe Ser Thr Ala Thr Ser Leu Ser Asp Leu Thr Ile Glu Ser
1650                1655                1660
Pro Pro Asn Glu Leu Ala Ala Gly Glu Gly Val Arg Gly Gly Ala Gln
1665                1670                1675                1680
Ser Gly Glu Phe Glu Lys Arg Asp Thr Ile Pro Thr Glu Gly Arg Ser
            1685                1690                1695
Thr Asp Glu Ala Gln Gly Gly Lys Thr Ser Ser Val Thr Ile Pro Glu
        1700                1705                1710
Leu Asp Asp Asn Lys Ala Glu Glu Gly Asp Ile Leu Ala Glu Cys Ile
    1715                1720                1725
Asn Ser Ala Met Pro Lys Gly Lys Ser His Lys Pro Phe Arg Val Lys
1730                1735                1740
Lys Ile Met Asp Gln Val Gln Gln Ala Ser Ala Ser Ser Ser Ala Pro
1745                1750                1755                1760
Asn Lys Asn Gln Leu Asp Gly Lys Lys Lys Lys Pro Thr Ser Pro Val
            1765                1770                1775
Lys Pro Ile Pro Gln Asn Thr Glu Tyr Arg Thr Arg Val Arg Lys Asn
        1780                1785                1790
Ala Asp Ser Lys Asn Asn Leu Asn Ala Glu Arg Val Phe Ser Asp Asn
    1795                1800                1805
```

-continued

```
Lys Asp Ser Lys Lys Gln Asn Leu Lys Asn Asn Ser Lys Asp Phe Asn
    1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
            1845                1850                1855

Ser Arg Asn Asp Ser Leu Ser Ser Leu Asp Phe Asp Asp Asp Val
        1860                1865                1870

Asp Leu Ser Arg Glu Lys Ala Glu Leu Arg Lys Ala Lys Glu Asn Lys
    1875                1880                1885

Glu Ser Glu Ala Lys Val Thr Ser His Thr Glu Leu Thr Ser Asn Gln
1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
            1925                1930                1935

Ser Lys Asp Ile Pro Asp Arg Gly Ala Ala Thr Asp Glu Lys Leu Gln
        1940                1945                1950

Asn Phe Ala Ile Glu Asn Thr Pro Val Cys Phe Ser His Asn Ser Ser
    1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
            2005                2010                2015

Thr Pro Val Cys Phe Ser Arg Asn Ser Ser Leu Ser Ser Leu Ser Ile
        2020                2025                2030

Asp Ser Glu Asp Asp Leu Leu Gln Glu Cys Ile Ser Ser Ala Met Pro
    2035                2040                2045

Lys Lys Lys Lys Pro Ser Arg Leu Lys Gly Asp Asn Glu Lys His Ser
    2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
            2085                2090                2095

Glu Asn Phe Asp Trp Lys Ala Ile Gln Glu Gly Ala Asn Ser Ile Val
        2100                2105                2110

Ser Ser Leu His Gln Ala Ala Ala Ala Cys Leu Ser Arg Gln Ala
    2115                2120                2125

Ser Ser Asp Ser Asp Ser Ile Leu Ser Leu Lys Ser Gly Ile Ser Leu
    2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
            2165                2170                2175

Glu Thr Lys Lys Ile Glu Ser Glu Ser Lys Gly Ile Lys Gly Gly Lys
        2180                2185                2190

Lys Val Tyr Lys Ser Leu Ile Thr Gly Lys Val Arg Ser Asn Ser Glu
    2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
```

-continued

```
                2225                2230                2235                2240
Ser Ser Thr Ser Pro Val Ser Lys Lys Gly Pro Pro Leu Lys Thr Pro
                2245                2250                2255
Ala Ser Lys Ser Pro Ser Glu Gly Gln Thr Ala Thr Thr Ser Pro Arg
                2260                2265                2270
Gly Ala Lys Pro Ser Val Lys Ser Glu Leu Ser Pro Val Ala Arg Gln
                2275                2280                2285
Thr Ser Gln Ile Gly Gly Ser Ser Lys Ala Pro Ser Arg Ser Gly Ser
                2290                2295                2300
Arg Asp Ser Thr Pro Ser Arg Pro Ala Gln Gln Pro Leu Ser Arg Pro
2305                2310                2315                2320
Ile Gln Ser Pro Gly Arg Asn Ser Ile Ser Pro Gly Arg Asn Gly Ile
                2325                2330                2335
Ser Pro Pro Asn Lys Ile Ser Gln Leu Pro Arg Thr Ser Ser Pro Ser
                2340                2345                2350
Thr Ala Ser Thr Lys Ser Ser Gly Ser Gly Lys Met Ser Tyr Thr Ser
                2355                2360                2365
Pro Gly Arg Gln Met Ser Gln Gln Asn Leu Thr Lys Gln Thr Gly Leu
                2370                2375                2380
Ser Lys Asn Ala Ser Ser Ile Pro Arg Ser Glu Ser Ala Ser Lys Gly
2385                2390                2395                2400
Leu Asn Gln Met Asn Asn Gly Asn Gly Ala Asn Lys Lys Val Glu Leu
                2405                2410                2415
Ser Arg Met Ser Ser Thr Lys Ser Ser Gly Ser Glu Ser Asp Arg Ser
                2420                2425                2430
Glu Arg Pro Val Leu Val Arg Gln Ser Thr Phe Ile Lys Glu Ala Pro
                2435                2440                2445
Ser Pro Thr Leu Arg Arg Lys Leu Glu Glu Ser Ala Ser Phe Glu Ser
                2450                2455                2460
Leu Ser Pro Ser Ser Arg Pro Ala Ser Pro Thr Arg Ser Gln Ala Gln
2465                2470                2475                2480
Thr Pro Val Leu Ser Pro Ser Leu Pro Asp Met Ser Leu Ser Thr His
                2485                2490                2495
Ser Ser Val Gln Ala Gly Gly Trp Arg Lys Leu Pro Pro Asn Leu Ser
                2500                2505                2510
Pro Thr Ile Glu Tyr Asn Asp Gly Arg Pro Ala Lys Arg His Asp Ile
                2515                2520                2525
Ala Arg Ser His Ser Glu Ser Pro Ser Arg Leu Pro Ile Asn Arg Ser
                2530                2535                2540
Gly Thr Trp Lys Arg Glu His Ser Lys His Ser Ser Ser Leu Pro Arg
2545                2550                2555                2560
Val Ser Thr Trp Arg Arg Thr Gly Ser Ser Ser Ser Ile Leu Ser Ala
                2565                2570                2575
Ser Ser Glu Ser Ser Glu Lys Ala Lys Ser Glu Asp Glu Lys His Val
                2580                2585                2590
Asn Ser Ile Ser Gly Thr Lys Gln Ser Lys Glu Asn Gln Val Ser Ala
                2595                2600                2605
Lys Gly Thr Trp Arg Lys Ile Lys Glu Asn Glu Phe Ser Pro Thr Asn
                2610                2615                2620
Ser Thr Ser Gln Thr Val Ser Ser Gly Ala Thr Asn Gly Ala Glu Ser
2625                2630                2635                2640
Lys Thr Leu Ile Tyr Gln Met Ala Pro Ala Val Ser Lys Thr Glu Asp
                2645                2650                2655
```

-continued

```
Val Trp Val Arg Ile Glu Asp Cys Pro Ile Asn Asn Pro Arg Ser Gly
        2660             2665             2670

Arg Ser Pro Thr Gly Asn Thr Pro Pro Val Ile Asp Ser Val Ser Glu
    2675             2680             2685

Lys Ala Asn Pro Asn Ile Lys Asp Ser Lys Asp Asn Gln Ala Lys Gln
2690             2695             2700

Asn Val Gly Asn Gly Ser Val Pro Met Arg Thr Val Gly Leu Glu Asn
2705             2710             2715             2720

Arg Leu Asn Ser Phe Ile Gln Val Asp Ala Pro Asp Gln Lys Gly Thr
        2725             2730             2735

Glu Ile Lys Pro Gly Gln Asn Asn Pro Val Pro Val Ser Glu Thr Asn
        2740             2745             2750

Glu Ser Ser Ile Val Glu Arg Thr Pro Phe Ser Ser Ser Ser Ser Ser
    2755             2760             2765

Lys His Ser Ser Pro Ser Gly Thr Val Ala Ala Arg Val Thr Pro Phe
    2770             2775             2780

Asn Tyr Asn Pro Ser Pro Arg Lys Ser Ser Ala Asp Ser Thr Ser Ala
2785             2790             2795             2800

Arg Pro Ser Gln Ile Pro Thr Pro Val Asn Asn Asn Thr Lys Lys Arg
        2805             2810             2815

Asp Ser Lys Thr Asp Ser Thr Glu Ser Ser Gly Thr Gln Ser Pro Lys
        2820             2825             2830

Arg His Ser Gly Ser Tyr Leu Val Thr Ser Val
        2835             2840
```

<210> SEQ ID NO 31
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (9)..(17)
<223> OTHER INFORMATION: N=A, T, C or G
<220> FEATURE:
<221> NAME/KEY: misc_feature
<222> LOCATION: (24)..(32)
<223> OTHER INFORMATION: N=A, T, C, or G
<220> FEATURE:
<221> NAME/KEY: misc_feature
<222> LOCATION: (39)..(41)
<223> OTHER INFORMATION: N=A, T, C  or G
<220> FEATURE:
<221> NAME/KEY: misc_feature
<222> LOCATION: (51)..(53)
<223> OTHER INFORMATION: N=A, T, C or G

<400> SEQUENCE: 31
cggaattcnn nnnnnnnaac agcnnnnnnn nnaatgaann ncaaagtctg nnntgaggat    60
cctca                                                              65

<210> SEQ ID NO 32
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (18)..(23)
<223> OTHER INFORMATION: N= A, T ,C or G

```
<220> FEATURE:
<221> NAME/KEY: misc_feature
<222> LOCATION: (33)..(38)
<223> OTHER INFORMATION: N=A, T, C or G
<220> FEATURE:
<221> NAME/KEY: misc_feature
<222> LOCATION: (42)..(50)
<223> OTHER INFORMATION: N=A, T, C or G

<400> SEQUENCE: 32
cggaattcga ctcagaannn nnnaacttca gannnnnnat cnnnnnnnnn gtctgaggat      60
cctca                                                                 65

<210> SEQ ID NO 33
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (9)..(53)
<223> OTHER INFORMATION: N=A, T, C or G

<400> SEQUENCE: 33
cggaattcnn nnnnnnnnn nnnnnnnnnn nnnnnnnnnn nnnnnnnnnn nnntgaggat      60
cctca                                                                 65

<210> SEQ ID NO 34
<211> LENGTH: 3
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: VARIANT
<222> LOCATION: (2)
<223> OTHER INFORMATION: X=any amino acid
<220> FEATURE:
<221> NAME/KEY: VARIANT
<222> LOCATION: (3)
<223> OTHER INFORMATION: X = Val or Leu or Ile

<400> SEQUENCE: 34

Ser Xaa Xaa
  1

<210> SEQ ID NO 35
<211> LENGTH: 3
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: VARIANT
<222> LOCATION: (1)
<223> OTHER INFORMATION: X = Ser or Thr
<220> FEATURE:
<221> NAME/KEY: VARIANT
<222> LOCATION: (2)
<223> OTHER INFORMATION: X = any amino acid

<400> SEQUENCE: 35

Xaa Xaa Val
  1

<210> SEQ ID NO 36
<211> LENGTH: 3
```

```
-continued

<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: VARIANT
<222> LOCATION: (2)
<223> OTHER INFORMATION: X = any amino acid

<400> SEQUENCE: 36

Ser Xaa Ile
  1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: VARIANT
<222> LOCATION: (2)
<223> OTHER INFORMATION: X = any amino acid
<220> FEATURE:
<221> NAME/KEY: VARIANT
<222> LOCATION: (3)
<223> OTHER INFORMATION: X = Ile or Leu

<400> SEQUENCE: 37

Thr Xaa Xaa
  1
```